United States Patent
Caizza et al.

(10) Patent No.: US 6,840,291 B2
(45) Date of Patent: Jan. 11, 2005

(54) ATTACHMENT FOR A MEDICAL DEVICE

(75) Inventors: Richard Caizza, Vernon, NJ (US);
Chad Smith, Oak Ridge, NJ (US);
John Pawlowski, Park Ridge, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 20 days.

(21) Appl. No.: 10/131,331

(22) Filed: Apr. 24, 2002

(65) Prior Publication Data
US 2002/0173753 A1 Nov. 21, 2002

Related U.S. Application Data

(63) Continuation-in-part of application No. 09/932,007, filed on Aug. 17, 2001, now Pat. No. 6,632,198, which is a continuation of application No. 09/419,184, filed on Oct. 15, 1999, now Pat. No. 6,368,303.

(51) Int. Cl.$^7$ .................................................. B65B 1/04
(52) U.S. Cl. ........................................... 141/25; 141/18
(58) Field of Search .................................. 141/18, 25–27; 604/181, 187, 192, 198, 218, 246, 239–243, 255, 248, 263, 284, 533–538, 403, 411, 414

(56) References Cited

U.S. PATENT DOCUMENTS

| | | | |
|---|---|---|---|
| 3,884,229 A | * 5/1975 | Raines et al. ............... 604/205 |
| 4,233,975 A | 11/1980 | Yerman | |
| 4,360,024 A | * 11/1982 | Wallace ....................... 604/256 |
| 4,629,455 A | * 12/1986 | Kanno ......................... 604/241 |
| 4,687,467 A | 8/1987 | Cygielski | |
| 4,729,401 A | * 3/1988 | Raines ......................... 137/512 |
| 4,838,863 A | 6/1989 | Allard et al. | |
| 4,838,869 A | 6/1989 | Allard | |
| 4,900,307 A | 2/1990 | Kulli | |
| 4,927,414 A | 5/1990 | Kulli | |
| 4,929,237 A | 5/1990 | Medway | |
| 4,946,446 A | 8/1990 | Vadher | |
| 4,955,870 A | 9/1990 | Ridderheim et al. | |
| 4,963,132 A | * 10/1990 | Gibson ........................ 604/256 |
| 4,966,593 A | 10/1990 | Lennox | |
| 4,973,316 A | 11/1990 | Dysarz | |
| 4,981,469 A | * 1/1991 | Whitehouse et al. ......... 604/86 |
| 4,991,629 A | * 2/1991 | Ernesto et al. .............. 138/89 |
| 4,994,034 A | 2/1991 | Botich et al. | |
| 4,998,927 A | * 3/1991 | Vaillancourt ................ 604/537 |
| 5,011,476 A | 4/1991 | Foster | |
| 5,013,301 A | 5/1991 | Marotta, Jr. et al. | |
| 5,019,044 A | 5/1991 | Tsao | |
| 5,045,063 A | 9/1991 | Spielberg | |
| 5,046,508 A | 9/1991 | Weissler | |
| 5,047,017 A | 9/1991 | Koska | |
| 5,047,021 A | * 9/1991 | Utterberg .................... 604/533 |

(List continued on next page.)

FOREIGN PATENT DOCUMENTS

| | | |
|---|---|---|
| GB | 2197792 A | 11/1986 |
| WO | WO 00/27450 | 11/1999 |

*Primary Examiner*—Nicholas D. Lucchesi
*Assistant Examiner*—Cris L. Rodriguez
(74) *Attorney, Agent, or Firm*—Jeanne P. Lukasavage; John L. Voellmicke

(57) ABSTRACT

A fluid transfer adapter for use with a syringe barrel having a collar with adapter engaging structure and a distally-facing frusto-conically shaped surface is disclosed. The adapter includes a hub having a proximally-facing frusto-conically shaped surface for mating with the frusto-conically shaped surface on the barrel, structure for threadably engaging the hub to the collar of the barrel so that the frusto-conically shaped surface of the hub contacts the frusto-conically shaped surface of the barrel to prevent liquid flow between the surfaces and a fluid transfer having a passageway therethrough, connected to the distal end of the hub so that the lumen is in fluid communication with a conduit in the hub. The passageway includes a frusto-conically shaped edge that aligns with the frusto-conically shaped edge of the barrel, when the adapter is connected to the barrel, thereby reducing waste space.

31 Claims, 31 Drawing Sheets

U.S. PATENT DOCUMENTS

| | | | |
|---|---|---|---|
| 5,049,133 A | | 9/1991 | Villen Pascual |
| 5,053,010 A | | 10/1991 | McGary et al. |
| 5,064,419 A | | 11/1991 | Gaarde |
| 5,066,286 A | * | 11/1991 | Ryan ........................... 604/240 |
| 5,071,413 A | * | 12/1991 | Utterberg ................... 604/533 |
| 5,084,018 A | | 1/1992 | Tsao |
| 5,084,029 A | | 1/1992 | Nacci Nee Tagliaferri |
| 5,085,640 A | | 2/1992 | Gibbs |
| 5,092,853 A | | 3/1992 | Couvertier, II |
| 5,098,405 A | * | 3/1992 | Peterson et al. ............ 604/247 |
| 5,099,992 A | * | 3/1992 | Heimreid ................... 206/366 |
| 5,114,410 A | | 5/1992 | Caralt Batlle |
| 5,180,369 A | | 1/1993 | Dysarz |
| 5,188,597 A | | 2/1993 | Sweeney et al. |
| 5,188,599 A | | 2/1993 | Botich et al. |
| 5,201,710 A | | 4/1993 | Caselli |
| 5,211,629 A | | 5/1993 | Pressly et al. |
| 5,232,447 A | | 8/1993 | Schwarz et al. |
| 5,232,456 A | | 8/1993 | Gonzalez |
| 5,267,961 A | | 12/1993 | Shaw |
| 5,267,976 A | | 12/1993 | Guerineau et al. |
| 5,342,308 A | | 8/1994 | Goschetti |
| 5,376,080 A | | 12/1994 | Petrussa |
| 5,385,551 A | | 1/1995 | Shaw |
| 5,389,076 A | | 2/1995 | Shaw |
| 5,395,337 A | | 3/1995 | Clemens et al. |
| 5,407,431 A | | 4/1995 | Botich et al. |
| 5,407,436 A | | 4/1995 | Toft et al. |
| 5,423,758 A | | 6/1995 | Shaw |
| 5,487,732 A | | 1/1996 | Jeffrey |
| 5,509,911 A | * | 4/1996 | Cottone et al. ............. 604/536 |
| 5,531,694 A | | 7/1996 | Clemens et al. |
| 5,533,970 A | | 7/1996 | Berger et al. |
| 5,542,927 A | | 8/1996 | Thorne et al. |
| 5,549,583 A | * | 8/1996 | Sanford et al. ............. 604/535 |
| 5,562,629 A | | 10/1996 | Haughton et al. |
| 5,573,510 A | | 11/1996 | Isaacson |
| 5,575,777 A | | 11/1996 | Cover et al. |
| 5,578,011 A | | 11/1996 | Shaw |
| 5,605,544 A | | 2/1997 | Tsao |
| 5,613,952 A | | 3/1997 | Pressly, Sr. et al. |
| 5,632,733 A | | 5/1997 | Shaw |
| 5,634,909 A | | 6/1997 | Schmitz |
| 5,637,092 A | | 6/1997 | Shaw |
| 5,643,211 A | | 7/1997 | Sadowski et al. |
| 5,665,075 A | | 9/1997 | Gyure et al. |
| 5,669,891 A | * | 9/1997 | Vaillancourt ................ 604/537 |
| 5,681,292 A | | 10/1997 | Tober et al. |
| 5,685,863 A | | 11/1997 | Botich et al. |
| 5,769,822 A | | 6/1998 | McGary et al. |
| 5,782,804 A | | 7/1998 | McMahon |
| 5,788,677 A | | 8/1998 | Botich et al. |
| 5,792,107 A | | 8/1998 | Petrocelli |
| 5,800,395 A | | 9/1998 | Botich et al. |
| 5,800,403 A | | 9/1998 | Pressly, Sr. et al. |
| 5,820,621 A | * | 10/1998 | Yale et al. .................. 604/411 |
| 5,843,034 A | | 12/1998 | Redfern et al. |
| 5,853,390 A | | 12/1998 | Freschi |
| 5,860,962 A | * | 1/1999 | Lewandowski et al. ..... 604/263 |
| 5,882,342 A | | 3/1999 | Cooper et al. |
| 5,885,257 A | | 3/1999 | Badger |
| 5,902,277 A | | 5/1999 | Jentzen |
| 5,908,408 A | | 6/1999 | McGary et al. |
| 5,910,131 A | | 6/1999 | McGary et al. |
| 5,919,166 A | | 7/1999 | McGary et al. |
| 5,921,959 A | | 7/1999 | McGary et al. |
| 5,921,960 A | | 7/1999 | McGary et al. |
| 5,921,961 A | | 7/1999 | McGary et al. |
| 5,935,104 A | | 8/1999 | Janek et al. |
| 5,984,898 A | | 11/1999 | Garvin |
| 6,004,278 A | | 12/1999 | Botich et al. |
| 6,010,486 A | | 1/2000 | Carter et al. |
| 6,036,674 A | | 3/2000 | Caizza et al. |
| 6,090,077 A | | 7/2000 | Shaw |
| 6,096,005 A | | 8/2000 | Botich et al. |
| 6,099,500 A | | 8/2000 | Dysarz |
| 6,171,287 B1 | * | 1/2001 | Lynn et al. .................. 604/256 |
| 6,183,440 B1 | | 2/2001 | Bell |
| 6,193,697 B1 | * | 2/2001 | Jepson et al. ............... 604/201 |
| 6,213,996 B1 | * | 4/2001 | Jepson et al. ............... 604/533 |
| 6,595,964 B2 | * | 7/2003 | Finley et al. ............... 604/246 |
| 2002/0115984 A1 | * | 8/2002 | Guala ......................... 604/533 |
| 2002/0147429 A1 | * | 10/2002 | Cowan et al. ............. 604/187 |
| 2003/0069545 A1 | * | 4/2003 | Arm ........................... 604/218 |
| 2003/0109853 A1 | * | 6/2003 | Harding et al. ............. 604/536 |

\* cited by examiner

ATTACHMENT FOR A MEDICAL DEVICE

This patent application is a continuation-in-part of U.S patent application Ser. No. 09/932,007 filed Aug. 17, 2001 now U.S. Pat. No. 6,632,198 which is a continuation of Ser. No. 09/419,184 filed Oct. 15, 1999, U.S. Pat. No. 6,368,303.

FIELD OF THE INVENTION

The present invention relates to syringes and needle assemblies. More particularly, the present invention relates to a syringe and needle assembly having structure allowing for the automatic withdrawal of the needle cannula into the syringe barrel after use and a method for making the needle assembly. The present invention also relates to adapters for use with such syringes.

BACKGROUND

In recent years there has developed an increased concern regarding the transfer of disease, infection or the like to syringe users and healthcare professionals who accidentally or through negligent handling, stick themselves with hypodermic needles while disposing of used hypodermic needle containing products. In many areas in a hospital, where needle cannula products are used, disposal bins are provided so that a syringe or other needle cannula product may be immediately discarded in a safe rigid container. However, there are areas of medical practice, such as emergency rooms, where disposal containers may not be readily available or practical, and where products having self-contained safety features are desirable. In theory, after such a syringe is used to inject medication or for another purpose, a safety device contained within the syringe or needle assembly is activated to prevent further contact with the sharp needle tip. One type of safety syringe includes structure which allows the withdrawal of the hypodermic needle into the syringe barrel to minimize the chance of further contact with the sharp needle tip.

One such prior art retractable needle syringe includes a frangible zone which allows the separation of the forward wall of the barrel, which is connected to the hypodermic needle, from the sidewall of the barrel. The syringe also contains structure on the interior of the forward wall and the exterior of the piston for selectively attaching the piston to the forward wall so that the user can forcibly twist the piston to break the frangible structure and draw the forward wall, including the hypodermic needle, into the syringe barrel. This design requires a compromise in the design of the syringe barrel. The barrel must be strong enough to remain intact during normal use yet weak enough to be sheared apart by any user regardless of strength.

The prior art also includes other retractable needle syringes. These syringes have structure that engages a needle carrier allowing the needle carrier to be forcibly disengaged from the syringe barrel, by action of the plunger rod, and withdrawn into the syringe barrel. Many prior art retractable needle syringes have deficiencies similar to that described above. In particular, the needle or the needle carrier of the retractable needle syringe must be securely held by the syringe barrel during normal use which often includes substantial hydraulic pressures experienced during injection, especially with highly viscous liquids, and forces including piercing rubber stoppers of medication vials. The syringe barrel must hold the needle carrier to a degree that it will not be overcome by the forces of normal use and will still be disengageable through forces applied to a plunger rod which extends from the open proximal end of the syringe barrel. Many prior art retractable needle syringe designs when made with sufficient strength to withstand the forces of normal use have a needle carrier which cannot be easily disengaged. On the other hand, easy disengagement of the needle or the needle carrier can lead to a structure which may not withstand the forces of normal use. This is especially true with needle carriers which are structured to allow a needle assembly to be installed and removed so that the user can select the hypodermic needle size at the time of use. These syringes must also resist the high torque and forces of needle installation and removal. In addition, retractable needle syringes require a two-handed withdrawal procedure which increases the difficulty of use.

The prior art also includes retracting needle syringes which include a spring loaded needle assembly which is held in position during normal use of the syringe assembly and a hollow plunger rod which is sealed during normal use of the syringe assembly so that medication may not enter the plunger rod cavity. These syringes must have structure to allow release of the spring-loaded needle and the opening of the plunger rod cavity so that the needle may enter the plunger rod cavity after the syringe is used for its intended purpose. The retracting needle syringes have similar design problems as those recited hereinabove for retractable needle syringes. In particular, the cavity in the plunger rod must be sealed so that medication cannot enter the plunger rod during use. This seal must sometimes withstand high hydraulic pressures when injecting relatively viscous medication through small needles and still be capable of being easily unsealed and to allow access by the needle assembly. Likewise, the needle assembly must be firmly held in place through the forces of injection and still be disengageable so that it may retract into the syringe barrel and into the plunger rod. Some of the prior art retracting needle syringes use plugs to cover the plunger rod cavity leading to an arguably difficult situation since the plug may fail during the injection process. Likewise, some use plugs to hold the needle assembly in place which can arguably become dislodged during use causing fear of the syringe. In addition, these designs do not allow for a replaceable needle assembly thus depriving the healthcare worker of the option of choosing the appropriate needle size for the injection or procedure being performed. Further, the demand for safety produces such as retracting needle syringes comes with the demand for products that cost little more than a standard syringe assembly. Prior art retracting needle assemblies have shortcomings in that they present designs that cannot be made for a cost that would allow their widespread use because many designs require very precise tolerances as to achieve reliability, and many require assembly processes which can damage the delicate tip of the needle cannula, leading to a high rejection rate.

Although the prior art teaches many different retractable needle syringes and retracting needle syringes having the capacity to withdraw or allow the needle to enter the syringe barrel or the plunger rod, there is still a need for a simple, straight-forward, reliable, easily fabricated retracting needle syringe having adequate structural integrity to withstand the forces of injection, while the spring can still be easily and intentionally released to allow the needle assembly to enter the plunger rod cavity. There is also a need for a retracting needle syringe having replaceable spring-loaded needle assemblies to allow selecting the proper needle size at the time of use and to facilitate prefilling. Also, there is a need for a retracting needle assembly that can be easily assembled in high volume without damaging the delicate cutting tip of the needle cannula.

SUMMARY OF THE INVENTION

An operable retracting needle assembly for use with a syringe barrel having an inside surface defining a chamber, an open proximal end, an open distal end including a cylindrical collar, and a plunger having a release element with a sharp distal edge includes: an outer hub having a proximal end, a distal end and a passageway therethrough, and an inner hub having a proximal end, a distal end and a conduit therethrough. The proximal end of the inner hub includes an inner portion and a dissociable outer portion connected to the inner portion. The dissociable outer portion of the inner hub is connected to the outer hub. The distal end of the inner hub is smaller than the passageway in the outer hub at its distal end and projects distally outwardly therefrom. A needle cannula having a distal end, a proximal end connected to the distal end of the inner hub, and a lumen therethrough. The connection is made so that the lumen is in fluid communication with the conduit of the inner hub. An energized spring is contained between the outer hub and the inner hub. Means for connecting the outer hub to the collar of the barrel such as through threaded engagement, adhesive, ultrasonic welding and the like is provided. The inner and outer hubs are configured so that distal motion of a plunger, having a release element with the sharp distal edge, in a barrel will cause the sharp distal edge of the release element to cut through the portion of the inner hub which separates the dissociable outer portion from the inner portion allowing the spring to move the needle cannula in a proximal direction.

An operable retracting needle assembly may also include a syringe barrel having an inside surface defining a chamber, an open proximal end and an open distal end including a cylindrical collar. The collar includes an outside surface and an inside surface. The outer hub is connected to the collar so that the cannula projects distally outwardly from the syringe barrel. A plunger is slidably positioned in fluid-tight engagement with the inside surface of the barrel. The plunger includes a proximal portion having a distal end with an elongated cavity therein, a release element having a sharp distal edge positioned on the distal end of the proximal portion, and a hollow distal portion releasably connected to the proximal portion and capable of telescopic motion with respect to the proximal portion. A cover element on the distal end of the distal portion seals the distal end of the distal portion. The proximal and distal portions of the plunger are connected so that when distal motion of the plunger with respect to the barrel causes the distal portion to contact structure in the distal end of the barrel additional force will cause the proximal portion of the plunger to separate from the distal portion of the plunger allowing the proximal portion to move distally so that the release element contacts and cuts through the cover element and the inner hub disconnecting the dissociable outer portion from the inner portion and allowing the spring to move the needle cannula far enough into the cavity of the proximal portion of the plunger rod so that the distal end of the cannula is positioned proximally of the distal end of the outer hub.

Another aspect of the present invention is a method of making an operable retracting needle assembly comprising the steps of: providing an outer hub having a proximal end, a distal end and a passageway therethrough; providing an inner hub having a proximal end, a distal end and a conduit therethrough; providing a needle cannula having a distal end, a proximal end, and a lumen therethrough; providing a coil compression spring; assembling the inner hub, the spring and the outer hub so that the spring is compressed and held within the outer hub by the inner hub being connected to the outer hub so that the distal end of the inner hub is accessible from the passageway at the distal end of the outer hub; positioning the proximal end of the cannula in the distal end of the conduit of the inner hub; and applying adhesive in the space between the conduit and the needle cannula.

A fluid transfer adapter for use with a syringe barrel having an inside surface defining a chamber, an open proximal end, an open distal end including a collar having adapter engaging structure and a distally-facing frusto-conically shaped surface comprises a hub having a proximal end, a distal end and a conduit therethrough. A proximally-facing frusto-conically shaped surface on the hub is provided for mating with the frusto-conically shaped surface on the syringe barrel. Means for threadably engaging the hub to the collar of the syringe barrel is provided so that the frusto-conically shaped surface of the hub contacts the frusto-conically shaped surface of the barrel to help prevent liquid flow between the surfaces during normal use of the syringe. A fluid transfer element including a cannula having a distal end, a proximal end and a lumen therethrough is provided. The proximal end of the cannula is connected to the distal end of the hub so that the lumen is in fluid communication with the conduit.

A fluid transfer adapter for use with a syringe barrel having an inside surface defining a chamber, an open proximal end, an open distal end including a collar having fluid transfer adapter engaging structure and a distally-facing frusto-conically shaped surface comprises a hub having a proximal end, a distal end, a conduit therethrough and a proximally-facing, frusto-conically shaped surface for mating with the frusto-conically shaped surface on the syringe barrel. Means for threadably engaging the hub to the collar of the syringe barrel is provided so that the frusto-conically shaped surface of the hub contacts the frusto-conically shaped surface of the barrel to prevent liquid flow between the surfaces. A fluid transfer element includes an elongate luer tip having a distal end, a proximal end and a passageway therethrough. The proximal end of the luer tip is connected to the distal end of the hub so that the passageway of the luer tip is in fluid communication with the conduit of the hub. A luer collar surrounds the luer tip and includes an inside surface with at least one thread on the inside surface. The luer tip and the luer collar are sized and shaped to engage a standard female luer fitting such as fittings found on hypodermic needle assemblies.

A fluid transfer apparatus comprises a syringe barrel and a fluid transfer adapter. The syringe barrel includes an inside surface defining a chamber, an open proximal end, an open distal end including a collar having adapter engaging structure and a distally-facing frusto-conically shaped surface. The fluid transfer adapter includes a hub threadably engaged with the collar of the syringe barrel. The hub includes a proximal end, a distal end, a conduit therethrough and a proximally facing frusto-conically shaped surface mating with the frusto-conically shaped surface of the barrel. The fluid transfer adapter also includes a fluid transfer element having a distal end, a proximal end and a passageway therethrough. The proximal end of the fluid transfer element is connected to the distal end of the hub so that the passageway is in fluid communication with the conduit. The fluid transfer element may include a variety of components including, but not limited to, an elongate cannula, an elongate luer tip having a tapered side wall and an elongate luer tip with a luer collar surrounding the tip having at least one thread on its inside surface and being sized and shaped to engage a standard female luer fitting. Fluid transfer apparatus may also include a plunger slidably positioned in fluid-tight engagement with the inside surface of the barrel. The plunger may include a proximal portion having a distal end and with an elongate cavity therein, a release element having a sharp distal edge on the distal end of the proximal portion, a hollow distal portion releasably connected to the proximal portion and capable of telescopic motion with respect to the proximal portion, and a cover element on the distal end of the distal portion sealing the distal end of the distal portion.

DETAILED DESCRIPTION

Figure 1:
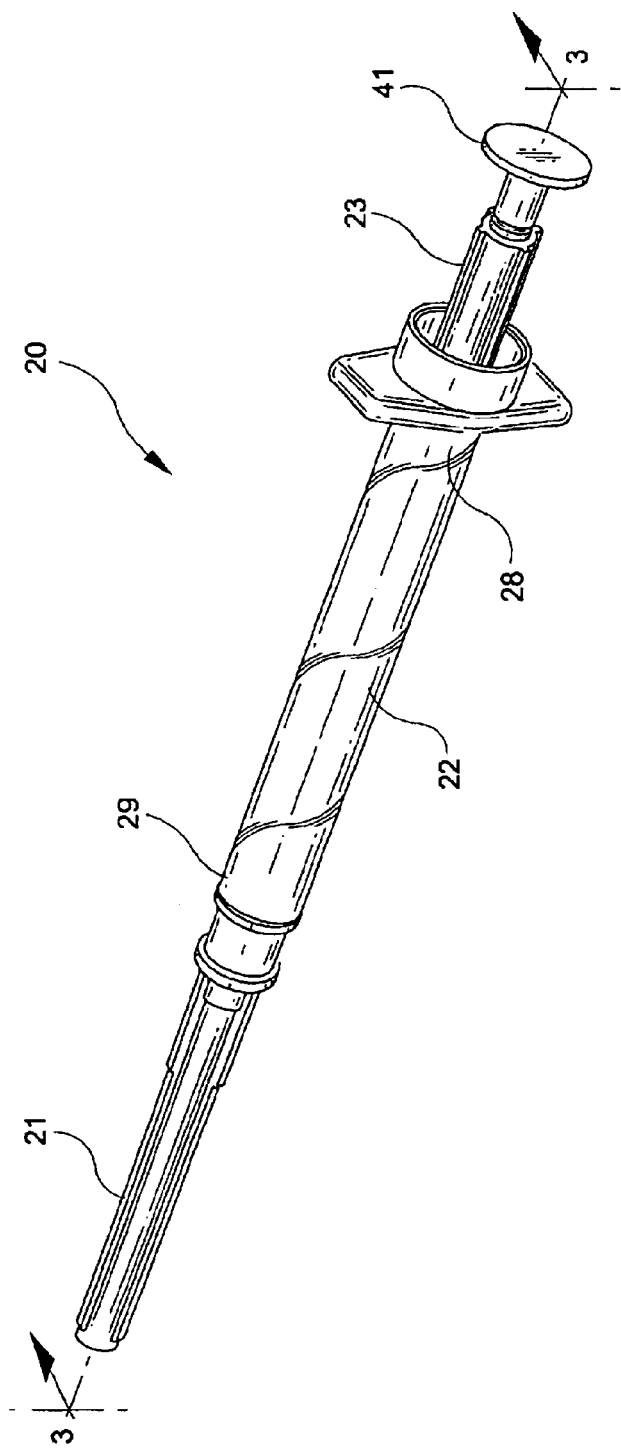
FIG. 1 is a perspective view of the retracting needle assembly and retracting needle syringe of the present invention.
Figure 2:
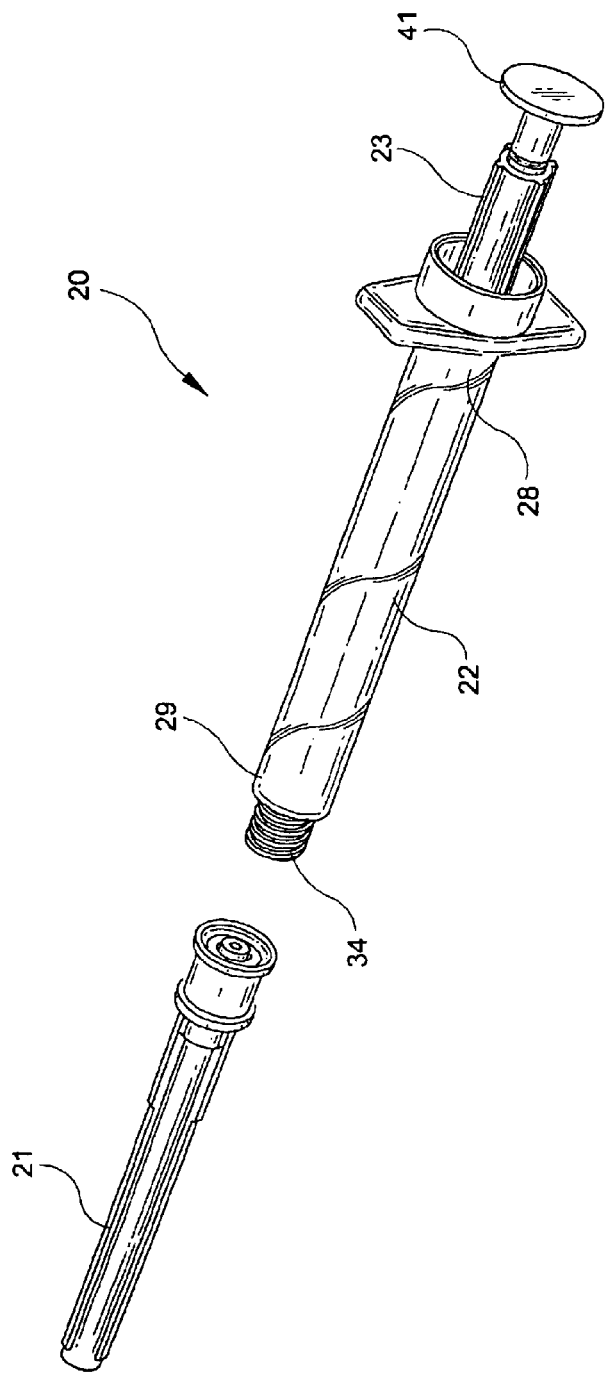
FIG. 2 is the syringe of FIG. 1 illustrating a replaceable needle assembly.
Figure 3:
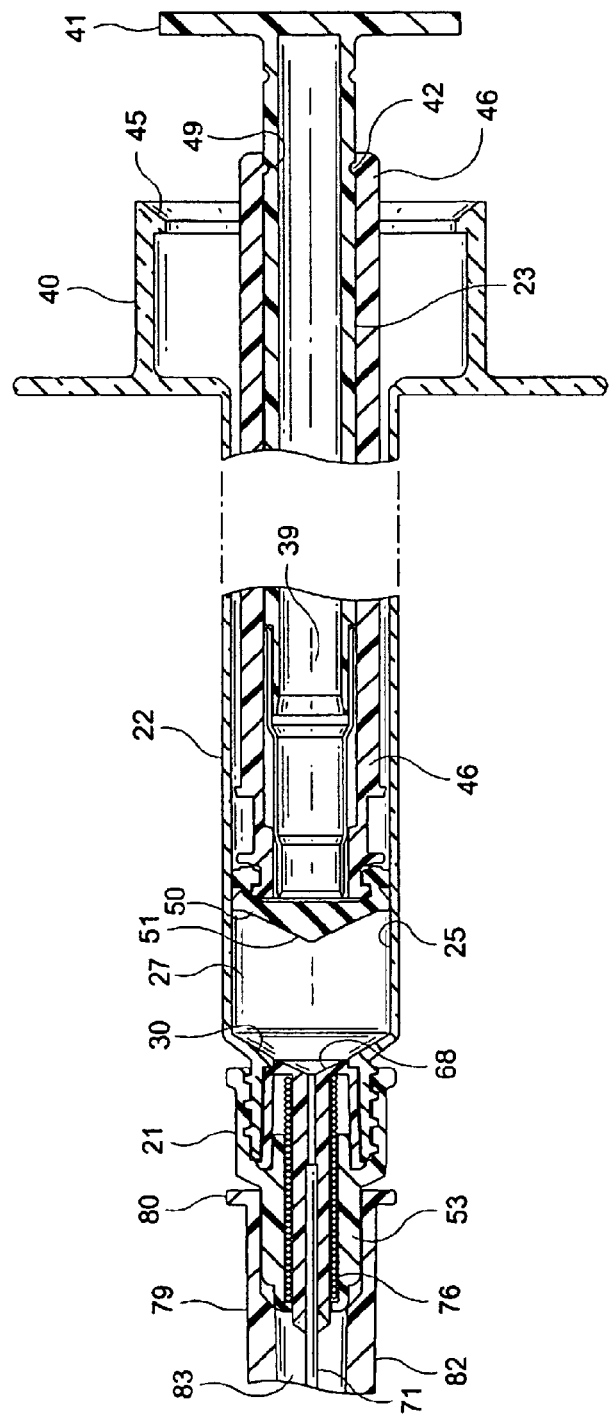
FIG. 3 is a cross-sectional view of the syringe and needle assembly of FIG. 1 taken along line 3—3.
Figure 4:
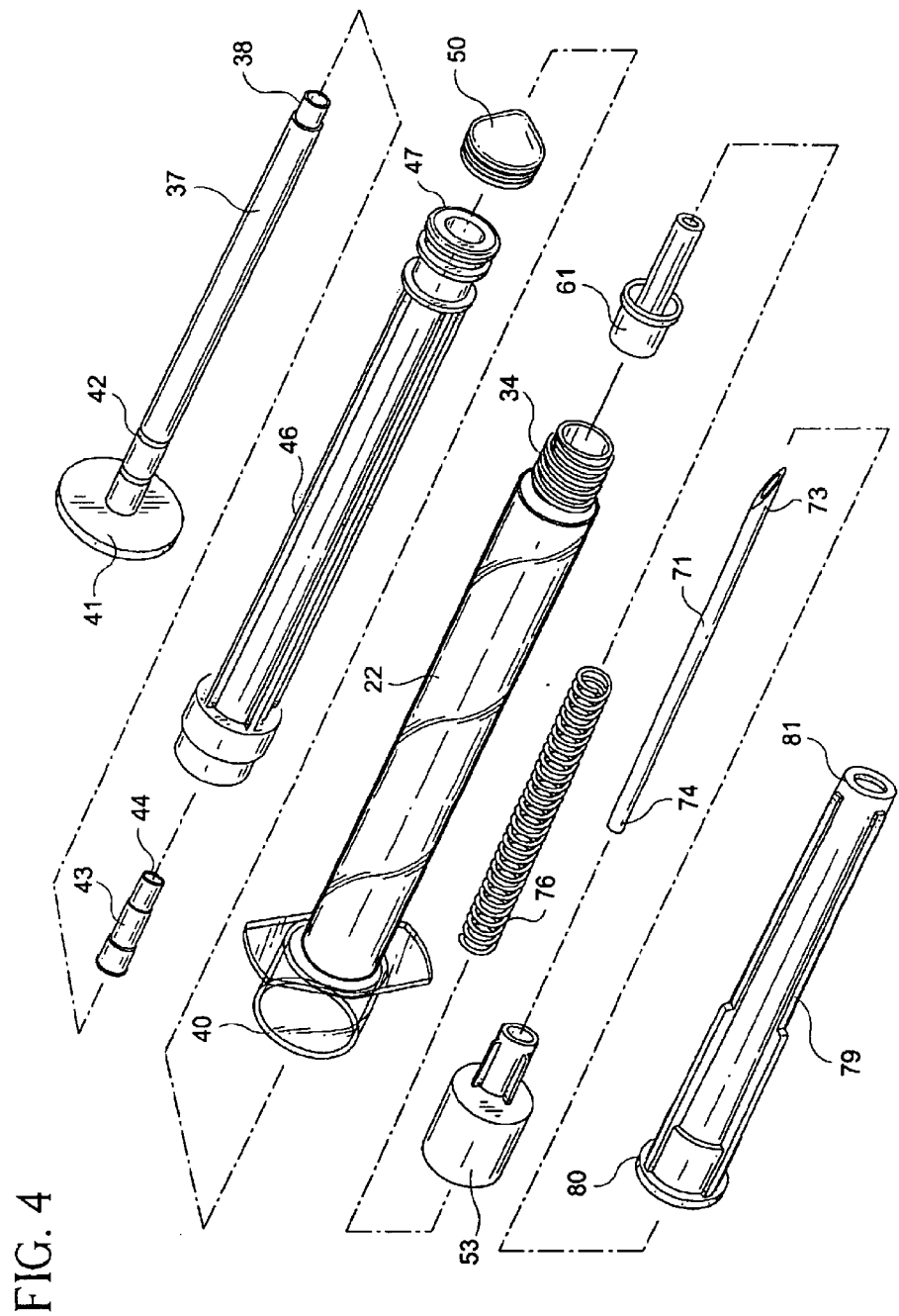
FIG. 4 is an exploded perspective view of the syringe and needle assembly of FIG. 1.
Figure 5:
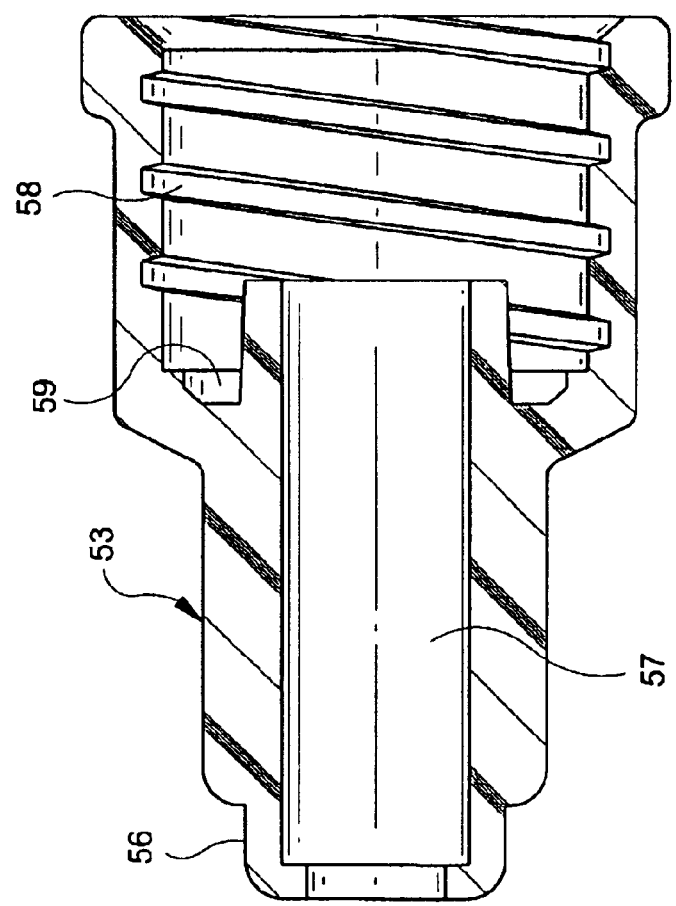
FIG. 5 is an enlarged cross-sectional view of the outer hub of the retracting needle assembly.
Figure 6:
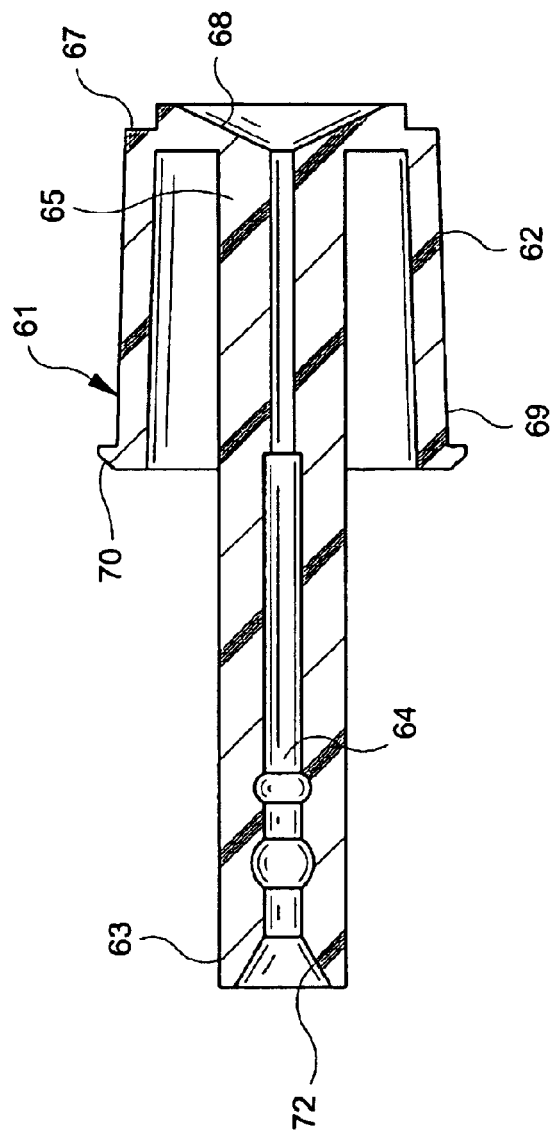
FIG. 6 is an enlarged cross-sectional view of the inner hub of the retracting needle assembly.
Figure 7:
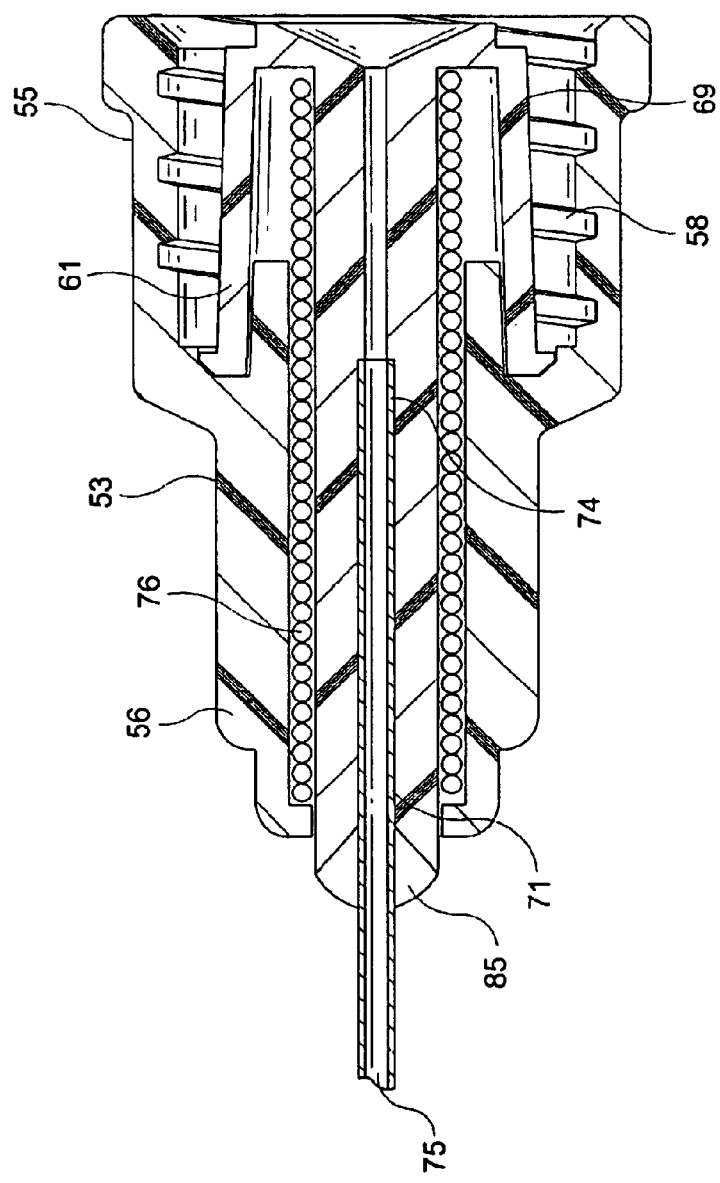
FIG. 7 is an enlarged cross-sectional view of the retracting needle assembly.
Figure 8:
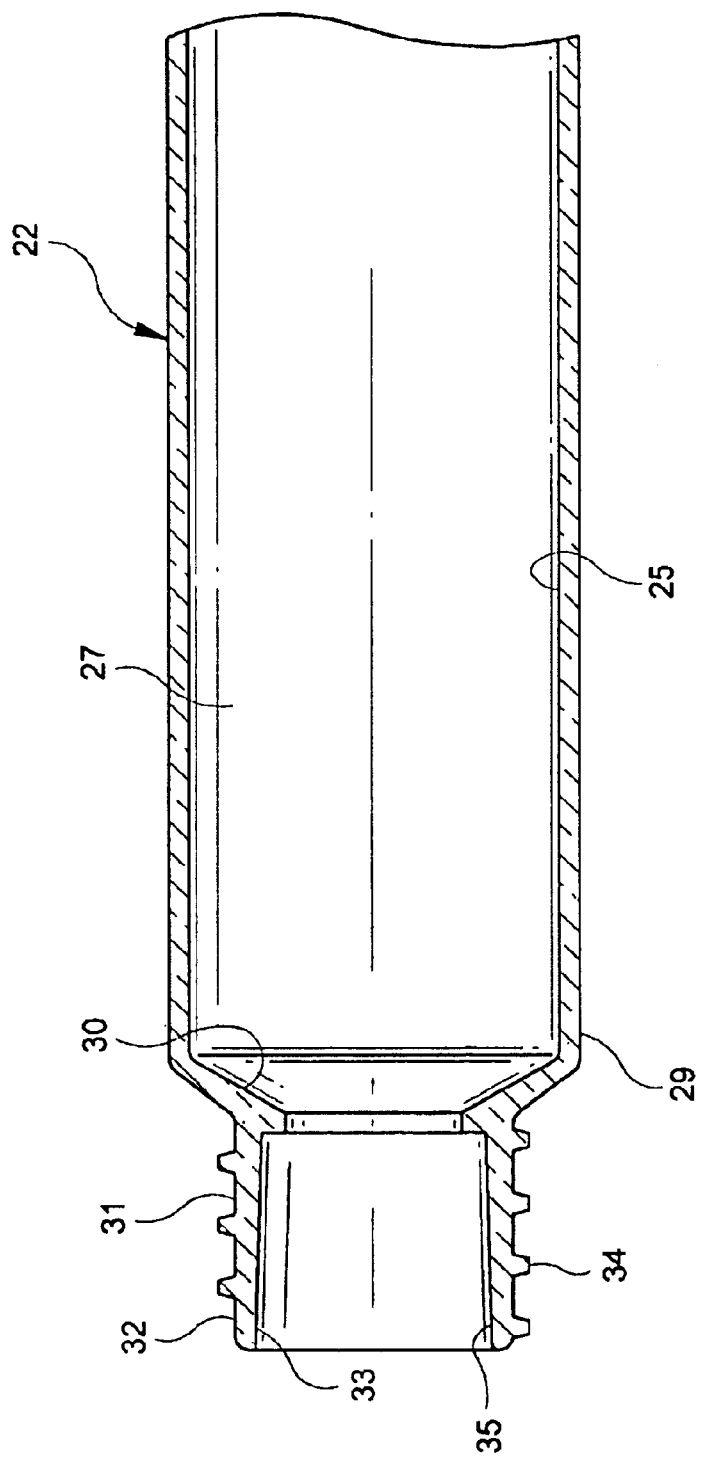
FIG. 8 is an enlarged cross-sectional view of the distal end of the syringe barrel.

While this invention is satisfied by embodiments in many different forms, there are shown in the drawings and will herein be described in detail, preferred embodiments of the invention with the understanding that the present disclosure is to be considered exemplary of the principles of the invention and not intended to limit the scope of the invention to the embodiments illustrated. The scope of the invention will be measured by the appended claims and their equivalents.

Referring to FIGS. 1–11, an operable retracting needle syringe 20 includes a retracting needle assembly 21, a syringe barrel 22 and a plunger 23. The barrel includes an inside surface 25 defining a chamber 27, an open proximal end 28 and an open distal end 29 including a cylindrical collar 31 having an outside surface 32 and an inside surface 33.

The plunger is slidably positioned in fluid-tight engagement with the inside surface of the barrel. The plunger includes a proximal portion 37 having a distal end 38 with an elongated cavity 39 therein. A release element 43 having a sharp distal edge 44 is positioned at distal end 38 of the proximal portion of plunger 23. A hollow distal portion 46 of plunger 23 is releasably connected to proximal portion 37 and capable of telescopic motion with respect to the proximal portion. A cover element on the distal portion seals a distal end 47. In this embodiment the cover element is stopper 50. It is preferred that the cover element be made of an elastomeric material selected from the group of thermoplastic elastomers, natural rubber, synthetic rubber and combinations thereof.

Retracting needle assembly 21 includes an outer hub 53 having a proximal end 55, a distal end 56 and a passageway 57 therethrough.

The retracting needle assembly also includes an inner hub 61 having a proximal end 62, a distal end 63 and a conduit therethrough 64. The inner hub includes an inner portion 65 and a dissociable outer portion 67 connected to the inner portion. The dissociable outer portion is connected to outer hub 53. Distal end 63 of the inner hub is smaller than passageway 57 of the outer hub at distal end 56 and is accessible therefrom and preferably projects distally outwardly therefrom.

A needle cannula 71 having a distal end 73, a proximal end 74 and a lumen 75 therethrough. The proximal end of the cannula is connected to distal end 63 of the inner hub so that the lumen is in fluid communication with conduit 64 of the inner hub. The distal end of the cannula preferably includes a sharp or sharpened distal tip.

An energized spring is contained between the outer and inner hubs and this preferred embodiment the energized spring is a compressed coil spring 76. Various spring types and elastomeric materials and the like can be used to provide a biasing force between the inner and outer hubs with the coil spring being merely representative of these many possibilities all of which are within the purview of the present invention. A coil spring is preferred because of its compact size and the ability to easily design the spring to provide the forces necessary for proper operation of the retractable needle assembly.

During assembly the coil spring is placed over the inner portion of the inner hub and then the distal end of the spring is positioned in the outer hub and the inner and outer hubs are moved toward each other to compress the spring and lock together through the action of annular locking projection 70 on the inner hub and annular locking recess 59 in the outer hub. When the inner hub and outer hub are joined, compressing the coil spring, annular locking projection on the inner hub snaps into annular locking recess 59 in the outer hub. The projection and the recess are shaped so that much less force is required to assemble the components than to reverse the process, thus providing for a permanent locked condition wherein the inner hub and the outer hub are inseparable during normal operating conditions. There are numerous ways to connect the inner and outer hub and the snap-fit arrangement taught herein is merely representative of all of these methods which are within the purview of the present invention. In particular, adhesives, separate metal locking clips, ultrasonic welding, crimping, internally molded locking structure and the like can be used to hold the inner hub and the outer hub together. An important advantage of the present invention, as will be explained in more detail hereinafter, is that the inner hub, the outer hub and the spring can be assembled before the needle cannula is added to the retracting needle assembly. A preferred way to connect the needle cannula to the retracting needle assembly is to place the proximal end of the needle cannula into the distal end of conduit 64 of the inner hub. An enlarged or irregular portion 72 at the distal end of conduit 64 provides a space for adhesive 85 to be placed around the outside of the needle cannula after it is positioned in the conduit.

The retracting needle assembly also includes means for connecting the outer hub to the collar of the syringe barrel. In this preferred embodiment, means for connecting includes structure providing for threadable engagement between the collar and the outer hub. In this preferred embodiment the structure for threadable engagement includes at least one thread 58 in passageway 57 of outer hub 53 and at least one thread 34 on outside surface 32 of the cylindrical collar. The ability to provide a needle assembly which is removably connected to the barrel is an important feature of this embodiment of the present invention. This feature allows flexibility to interchange needle assemblies and syringes to obtain an appropriately sized needle and syringe combination for the desired drug type and injection site. In addition, the structure of the preferred embodiment allows the installation and removal of the needle assembly from the barrel using the same motions required for installation and removal of a standard hypodermic needle from a standard hypodermic syringe so that no additional training is required for the health care worker.

Another important feature of the present invention is providing a retracting needle syringe with low dead space. This means that almost all of the medication in the chamber is expelled from the syringe during the injection process. Many prior art retractable and retracting needle syringes have structure protruding into the chamber for holding and/or releasing the retracting or retractable needle. Much of the medication surrounding these structures is lost and will not be delivered because needle retraction will have begun while the medication is still in the barrel. To minimize medication loss in retracting needle syringes having structure protruding into the chamber the user could begin the needle retracting process while the needle is still within the patient. The needle could still come out of the patient while medication is being delivered and there is a potential for injury to the patient if the needle is moved laterally as the result of the force being applied to initiate the needle retraction process.

To optimize the feature of low dead space in the present invention, the preferred embodiment includes a frusto-conically shaped surface 68 at proximal end 62 of the inner hub which is preferably a recess. This surface is adapted to mate a conically-shaped surface 51 on stopper 50. Surface 51 is preferably a projection. As the medication is driven from the chamber through the lumen of the cannula stopper 50 approaches the distal end of the syringe barrel until the frusto-conically shaped surface on the stopper approaches very closely and preferably contacts the frusto-conically shaped surface on the inner hub. The drawings show a slight gap between these two elements for clarity purposes only, and it is preferred that at the completion of the plunger stroke the surfaces are touching. Also, the distal end of the syringe barrel includes a frusto-conically shaped surface 30 which also approaches and preferably touches the stopper when the plunger is in its distal-most position with respect to delivering medication from the chamber.

The structure for threadable engagement between the collar and the outer hub can include a wide variety of thread-like and bayonette-type structures including a thread on the outside surface of the collar and a thread follower projection on the inside surface of the outer hub which will follow the collar thread as the hub is screwed onto the collar. This structure is similar to the well-known locking luer-type needle assembly and syringe combinations wherein the syringe collar has a thread on its inside surface and the needle assembly has two outwardly directed projections on the base of its hub for allowing the hub follow the threads of the collar as it is screwed onto the luer tip and collar. Also, the inside of the collar can be threaded in the outside of the outer hub can have thread followers.

One of the issues not well addressed by the prior art is leakage. During use, the contents of the syringe are subject to high pressures, both positive and negative, when trying to draw in and deliver medications, especially with viscous medications. To help prevent leakage, preferably without having to use a gasket, the preferred embodiment includes tapered cylindrical surface 69 on inner hub 61 and tapered cylindrical surface 35 on the inside of cylindrical collar 31 of the barrel. When the retracting needle assembly engages the collar of the barrel, the tapered cylindrical surface 35 on the collar engages tapered cylindrical surface 69 on the inner hub to seal the interface between the hub and the collar to prevent leakage during normal use.

The present invention provides a clear departure and improvement over the prior art by offering features such as leakage protection without the use of gaskets, and low dead-space in combination with a removable retracting needle assembly.

Retracting needle assembly 21 preferably, but not necessarily, includes an elongated needle shield 79 having an open proximal end 80, a distal end 81 and a sidewall 82 therebetween defining a recess 83 in the shield. The shield removably engages the outer hub and covers the needle cannula. The shield helps protect the needle cannula from contamination before use. In this embodiment, the shield preferably frictionally engages portions of outer hub 53. However, it is within the purview of the present invention to provide a shield which engages portions of the syringe barrel.

Figure 9:
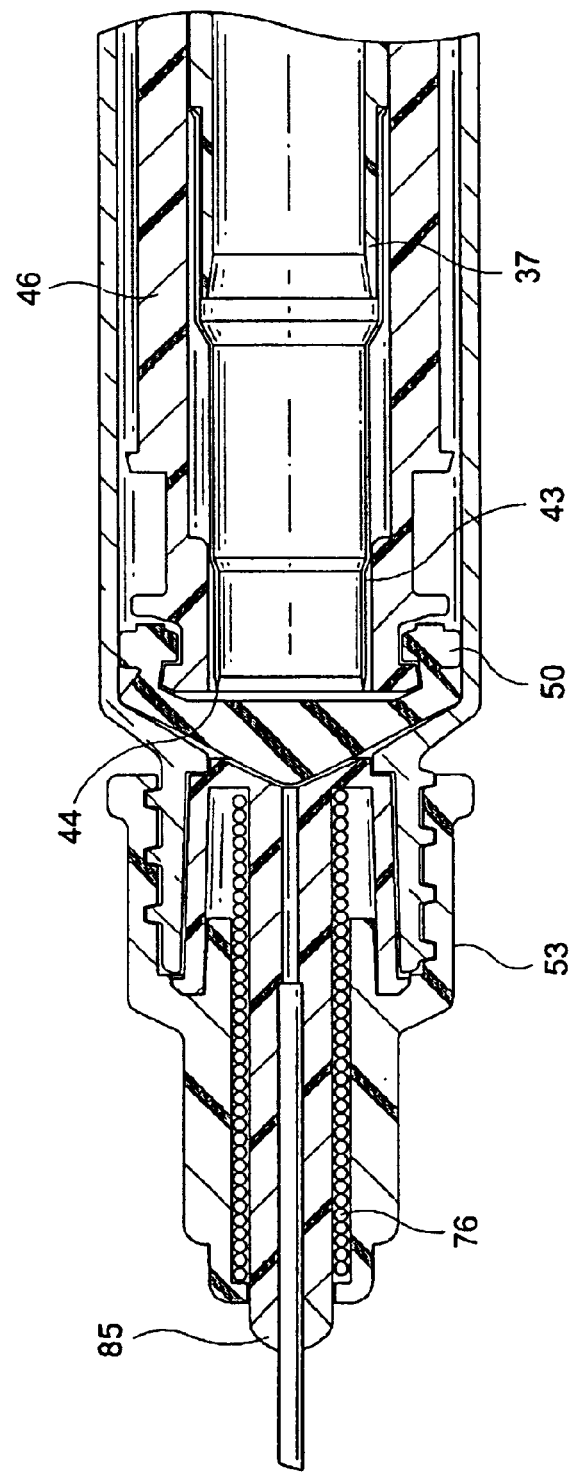
FIG. 9 is a cross-sectional view of the distal end of the syringe and retracting needle assembly of FIG. 1 illustrating the syringe after the liquid contained therein has been delivered.
Figure 10:
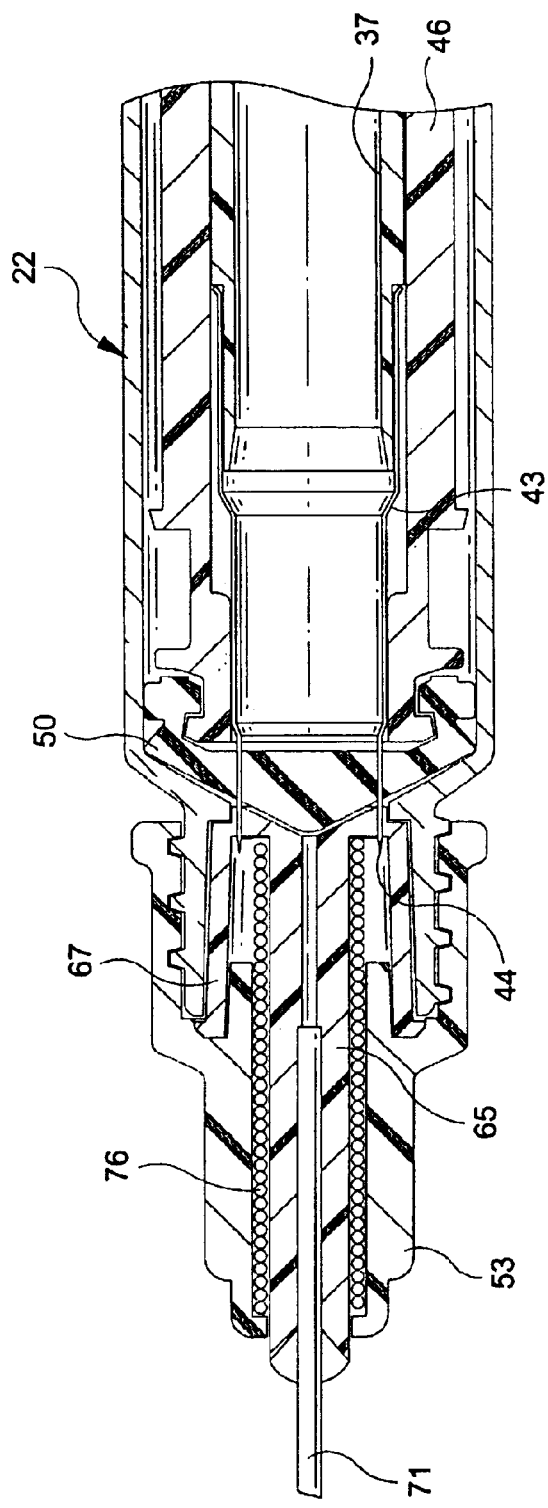
FIG. 10 illustrates the syringe of FIG. 9 when the proximal and distal portions of the plunger rod have separated and release element has cut through the stopper and portions of the inner hub.
Figure 11:
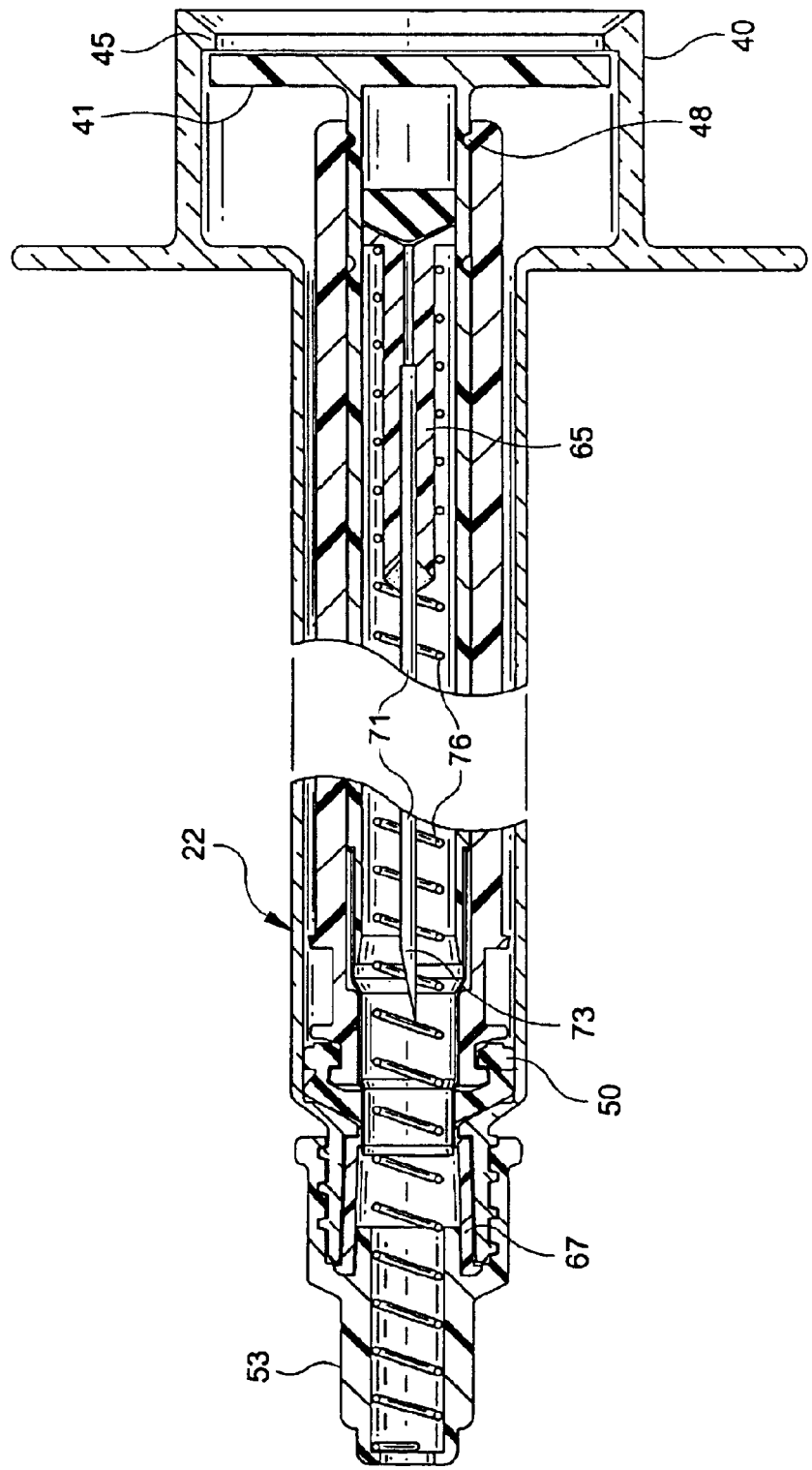
FIG. 11 illustrates the syringe of FIG. 10 when the release element has cut completely through the inner hub and the needle has retracted into the plunger.

In use, the retracting needle assembly of the present invention can be removably connected to syringe barrel 22 containing plunger 23. Needle shield 79 can now be removed from the retracting needle assembly thus exposing the needle cannula for use. The retracting needle syringe can be filled using known methods such as withdrawing injectable liquid from a vial having a pierceable stopper. A syringe may then be used to inject liquid into a patient, an I.V. set, a catheter or other suitable device. After the liquid in the chamber is injected or otherwise delivered, the distal end of the stopper will be contacting the distal end of the barrel chamber as best illustrated in FIG. 9. At this point, the user can apply additional distally directed axial force to the proximal end of the plunger to bottom out the stopper on the distal end of the barrel chamber and to cause the disengagement of the proximal portion 37 of the plunger from distal portion 46 of the plunger. Because the connection between the proximal portion of the plunger and the distal portion of the plunger is broken or overcome, the proximal portion will move distally within the distal portion and along the barrel advancing release element 43 so that its sharp distal end will press on and cut through stopper 50 and through the inner hub between inner portion 65 and dissociable outer portion 67, as best illustrated in FIG. 10. Application of a distally directed force to the plunger which causes the release element to cut completely through the inner hub, will allow the spring to propel the inner portion of the inner hub along with the needle cannula into the elongated cavity of the plunger as best illustrated in FIG. 11. The used needle cannula is now safely contained within the syringe assembly and ready for safe disposal.

Another feature of the syringe barrel and plunger of the present invention is proximally facing circular wall 40 on the proximal end of the barrel which is slightly larger than flange 41 on the proximal end of the plunger so that when the plunger reaches its furthest distal position with respect to the barrel, the flange 41 is within the circular wall 40 thus preventing the user from attempting to pull the plunger in a proximal direction in an attempt to re-expose the needle. A mechanical interference such as an overlap or snap fit structure can also be provided to further hold the flange Inside the circular wall. In this preferred embodiment, inwardly directed ledge 45 is provided to hold the plunger In the barrel after the needle cannula has been retracted. Also, a second groove 48 on the plunger rod can be used to help hold the plunger in the barrel after needle retraction. This second groove is preferably used if an inwardly directed ledge or other structure is not used on circular wall 40. When using second annular groove 48, annular projection 49 on the plunger will engage groove 48 after needle retraction. This engagement will hold the proximal portion of the plunger to the distal portion of the plunger, wherein the distal portion of the plunger will be held in the barrel by the friction of the stopper.

In this preferred embodiment the releasable connection between proximal portion 37 of the plunger and distal portion 46 of the plunger which allows the telescopic relative motion between the two plunger portions is provided by a snap-fit arrangement between the proximal portion of the plunger and the distal portion of the plunger. In particular, an annular projection 49 on the inside of the proximal end of the distal portion 46 of the plunger engages an annular groove 42 on the proximal end of proximal portion 37 of the plunger. When sufficient axial force is applied, annular projection 49 disengages from annular groove 42 allowing the distal end of the release element to cut through the stopper and the inner hub between the dissociable outer portion and the inner portion. There are numerous structures and materials and elements which can provide for a releasable connection between the proximal and distal portions of the plunger with the structure taught hereinabove being merely representative of the many possibilities all of which are within the purview of the present invention. In particular, any combination of projections and/or recesses and/or discontinuities on the proximal portion and the distal portion can accomplish a similar result. Also, the connection can also be breakable as well as disengageable such as by use of a frangible adhesive between the two elements or molding the elements as an integral structure containing a brittle plastic projection or projections which join the elements and can be broken with a force applied to the plunger. A breakable connection can also be made by connecting the elements with a shear pin. A shear pin made be made of plastic with one or more notches or stress risers suitably placed to cause breaking at the desired force levels. A breakable connection may also be accomplished similar to the snap fit arrangement but designing the various projections and recesses to fail upon reaching the desired stress level.

Figure 12:
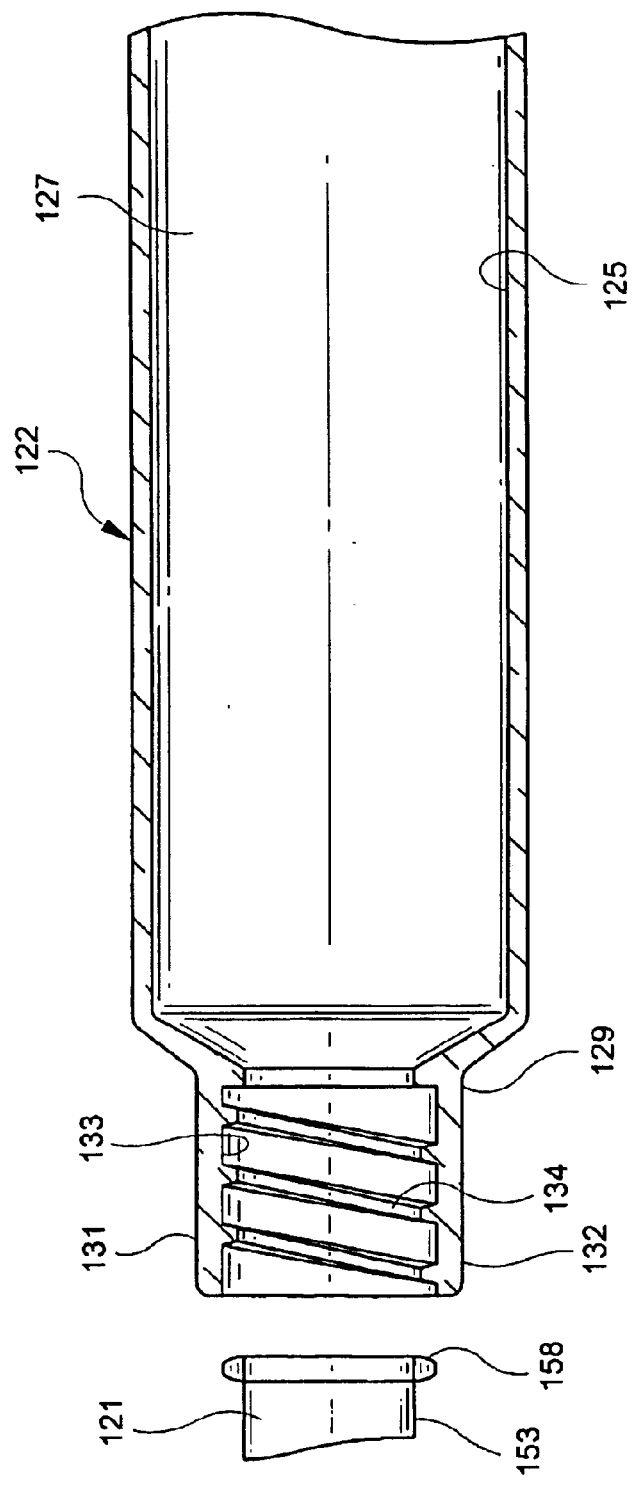
FIG. 12 is an alternative embodiment of the retracting needle assembly and syringe of the present invention.
Figure 13:
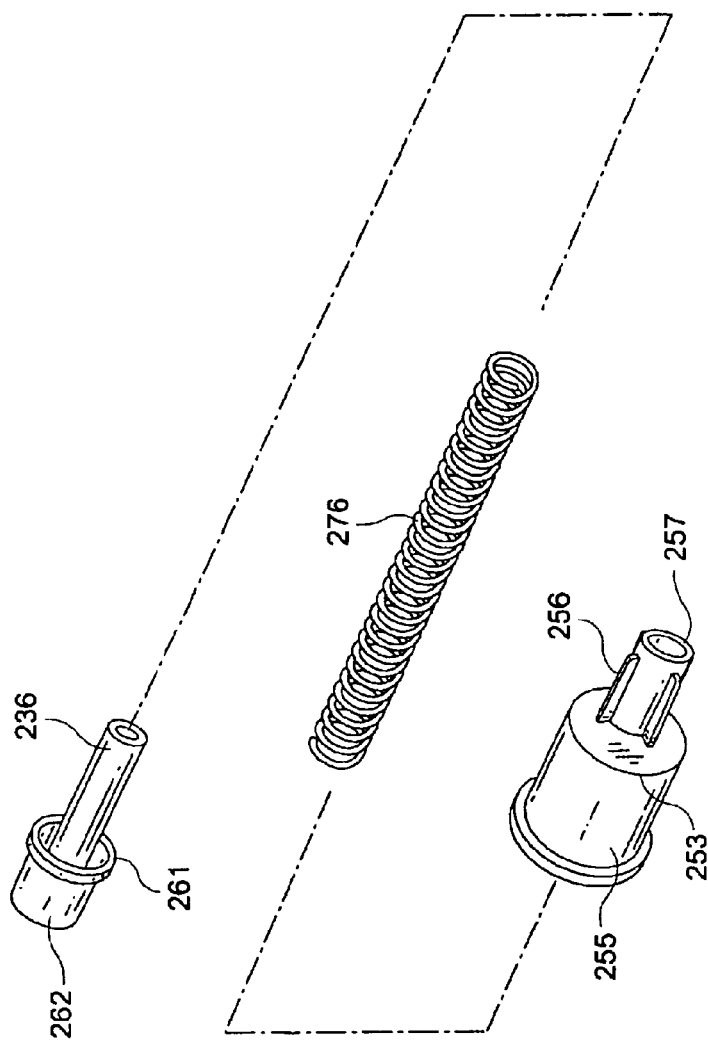
FIGS. 13–17 illustrate a method of making a retracting needle assembly of the present invention.

FIG. 12 illustrates an alternative embodiment of the present invention which functions similarly to the embodiment of FIGS. 1–11 except that means for connecting the outer hub to the collar. In particular, syringe barrel 122 includes an inside surface 125 defining a chamber 127, an open distal end 129, an open proximal end (not shown) and a cylindrical collar 131. The cylindrical collar includes an outside surface 132 and an inside surface 133. The inside surface includes at least one thread 134. A retracting needle assembly 121 includes an outer hub 153 having at least one, and in this preferred embodiment two radially directed outwardly projecting tabs sized and shaped to engage thread 134 so that the retracting needle assembly can be releasably engaged with the syringe barrel through rotational motion of the needle assembly relative to the barrel.

It is also within the purview of the present invention to include means for connecting the outer hub to the collar which is permanent rather than removably engageable. For example, the outer hub can be attached to the collar using adhesive or ultrasonic welding, retaining clips or a one-way snap-fit arrangement that renders the assembly irreversible under normal use. Such structures fall within the purview of the prevent invention.

Referring to FIGS. 13–17, another aspect of the present invention includes a method of making an operable retracting needle assembly. Many prior art retracting needle syringes have a major deficit in that their manufacture requires the needle to be assembled to the needle hub first and then the needle assembly including the needle and the hub is joined with the spring and outer hub or similar structures by placing the spring over the needle and the outer hub over the sharp tip of the needle. This is a difficult task and nearly impossible under high volume manufacturing since the potential for damaging the fragile sharpened distal end of the needle cannula is great. Consequently, these designs may become prohibitively expensive to make under mass production circumstances or yield an unacceptable level of damaged needles which are unsuitable for their purpose or at the very least very painful to the patient. A major improvement provided by the present invention is overcoming the aforementioned shortcomings of prior art retractable needle syringes and retractable needles. The present invention allows the assembly of the inner and outer hub and the spring before the addition and connection of the sharpened needle cannula. This allows the retracting needle assembly of the present invention to be manufactured in a similar manner to conventional needle assemblies wherein the needle is attached to the finished hub after which there are no further assembly steps but for the application of a needle shield.

Figure 14:
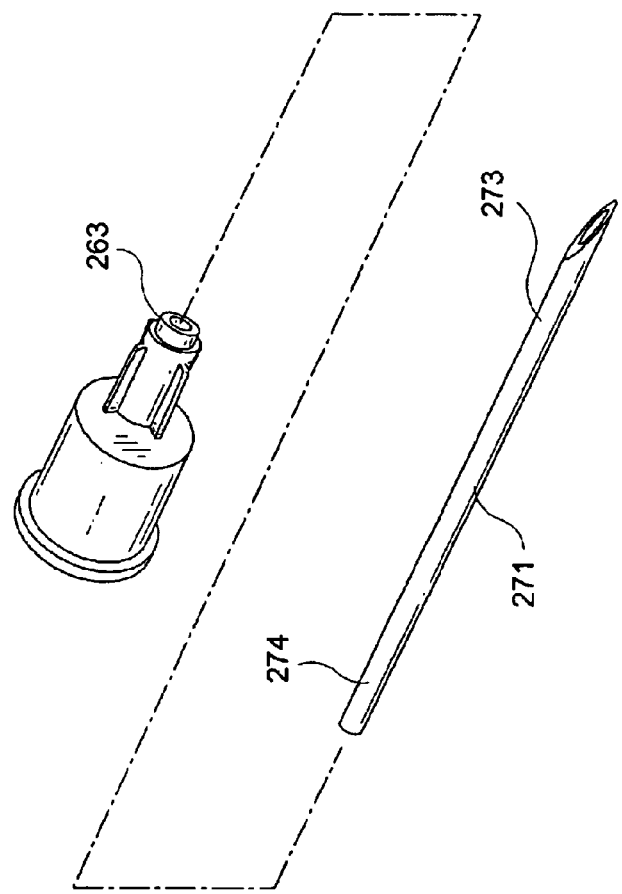
Figure 15:
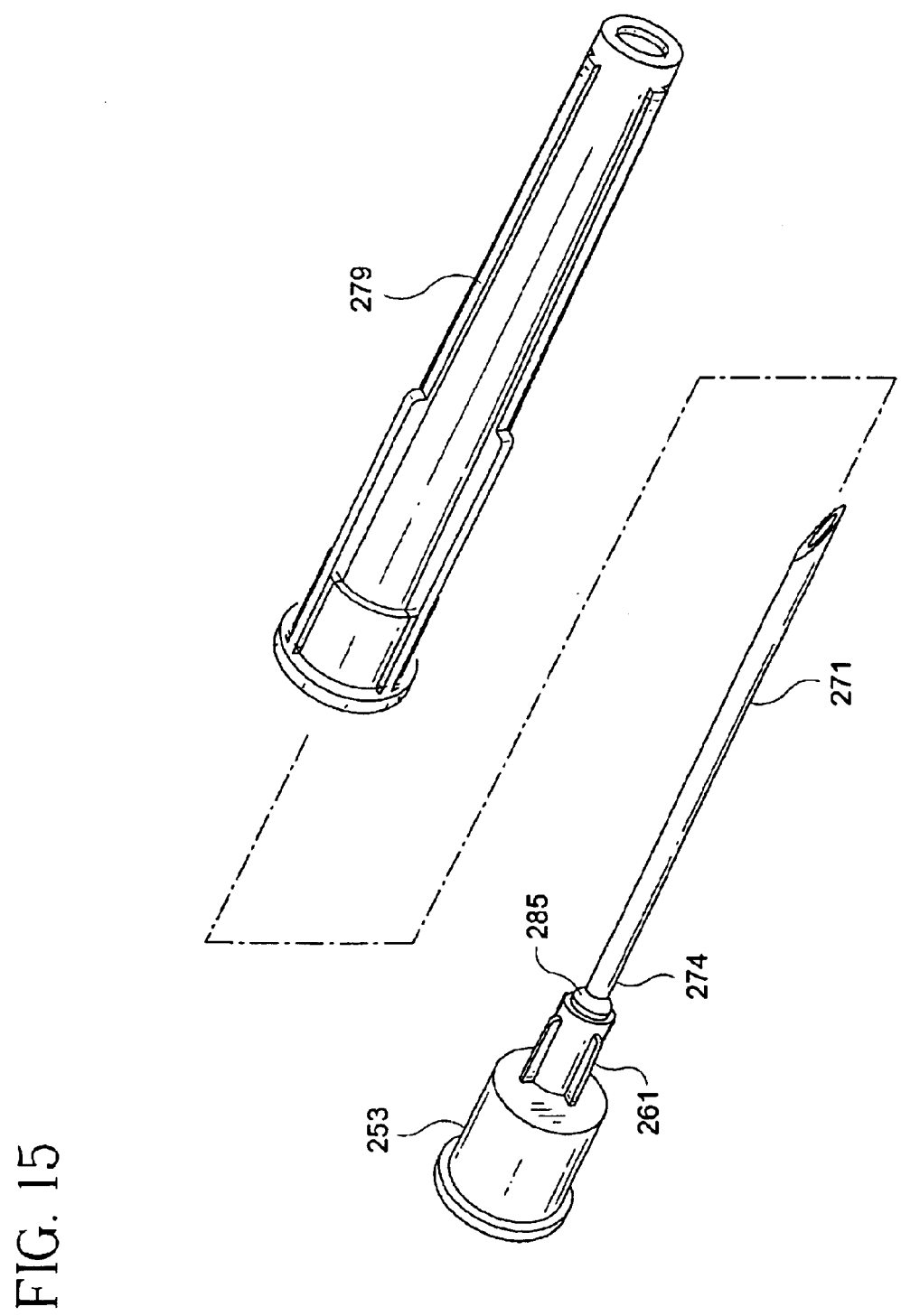
Figure 16:
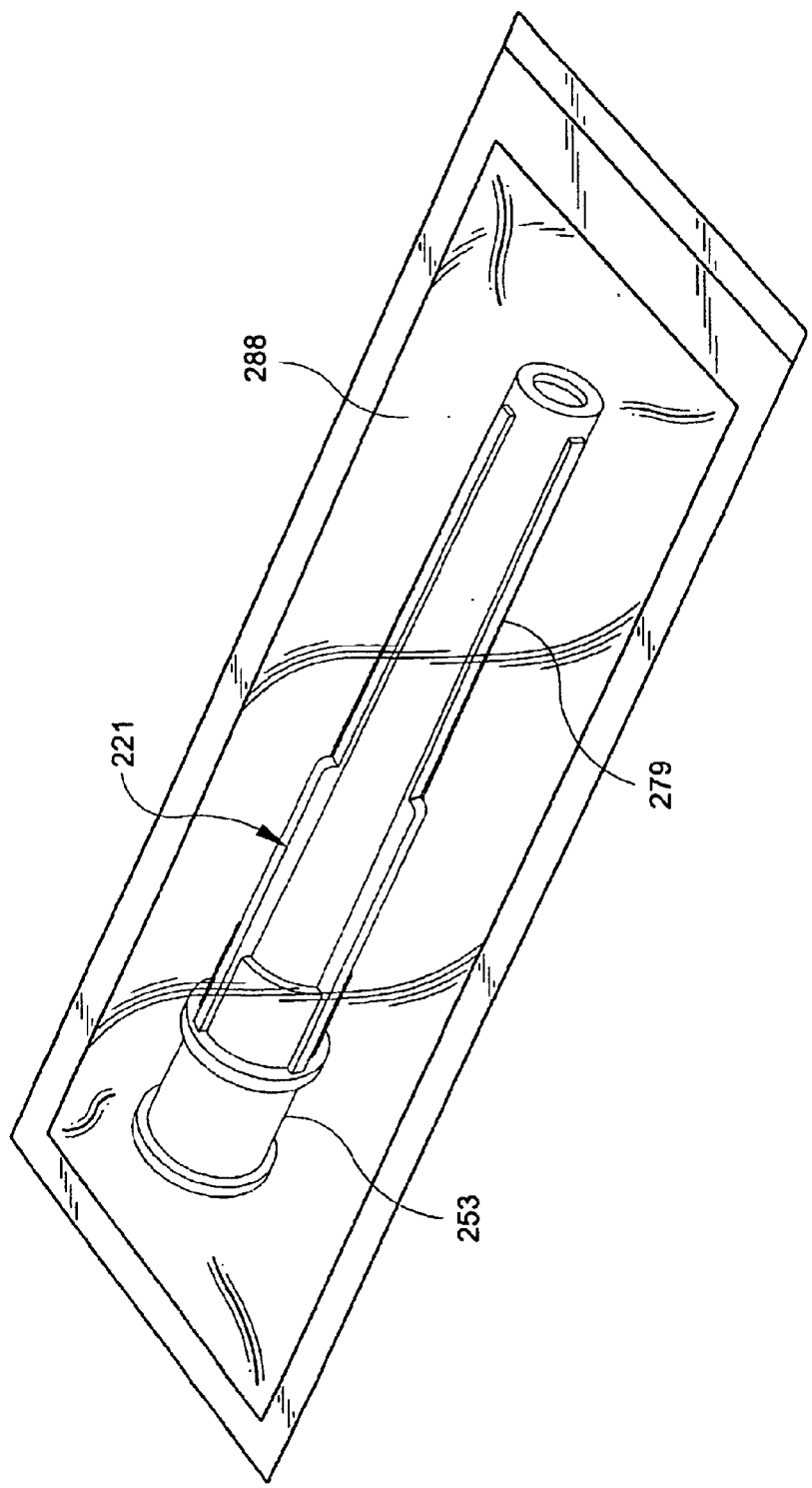
Figure 17:
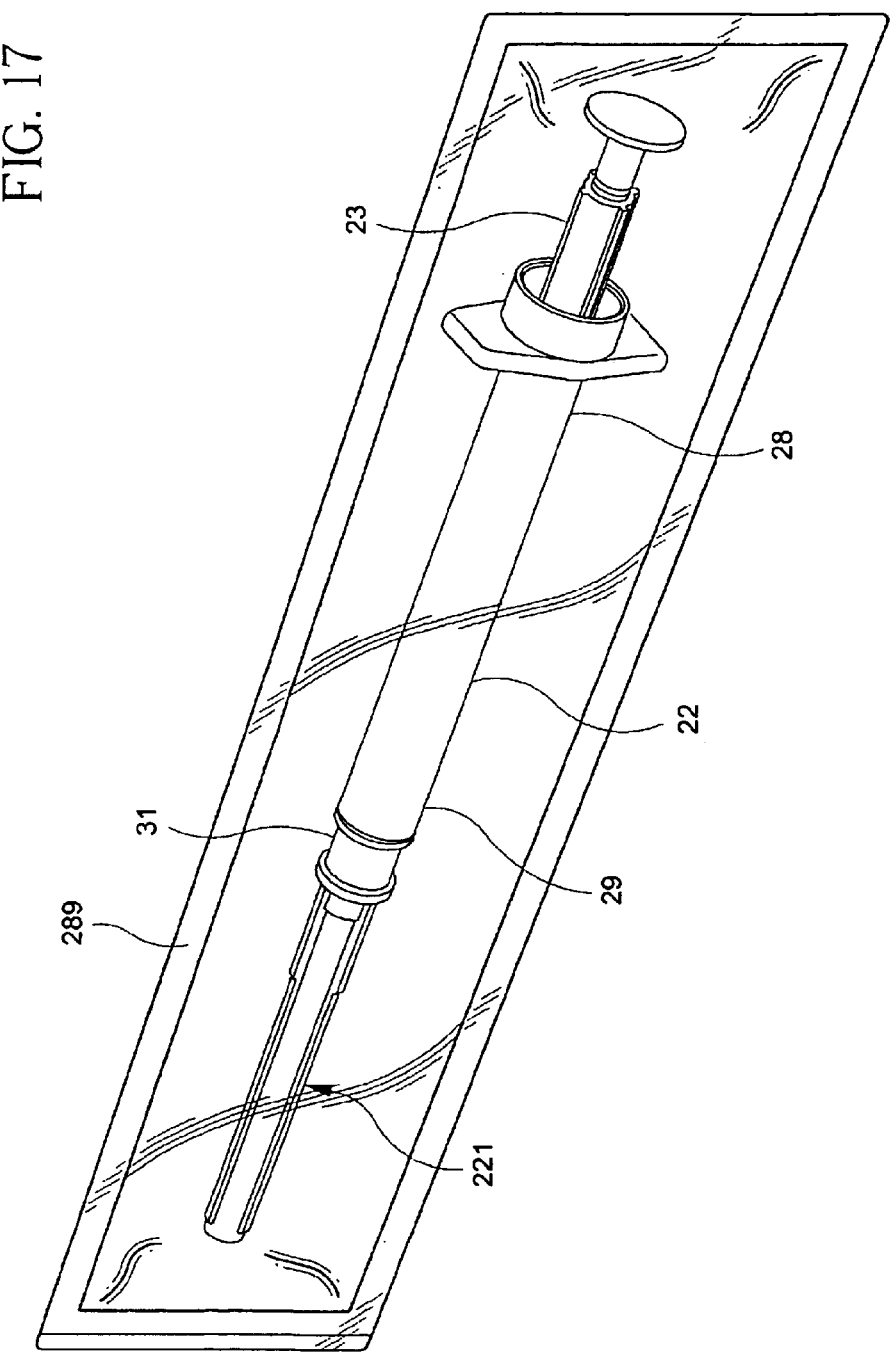
Figure 18:
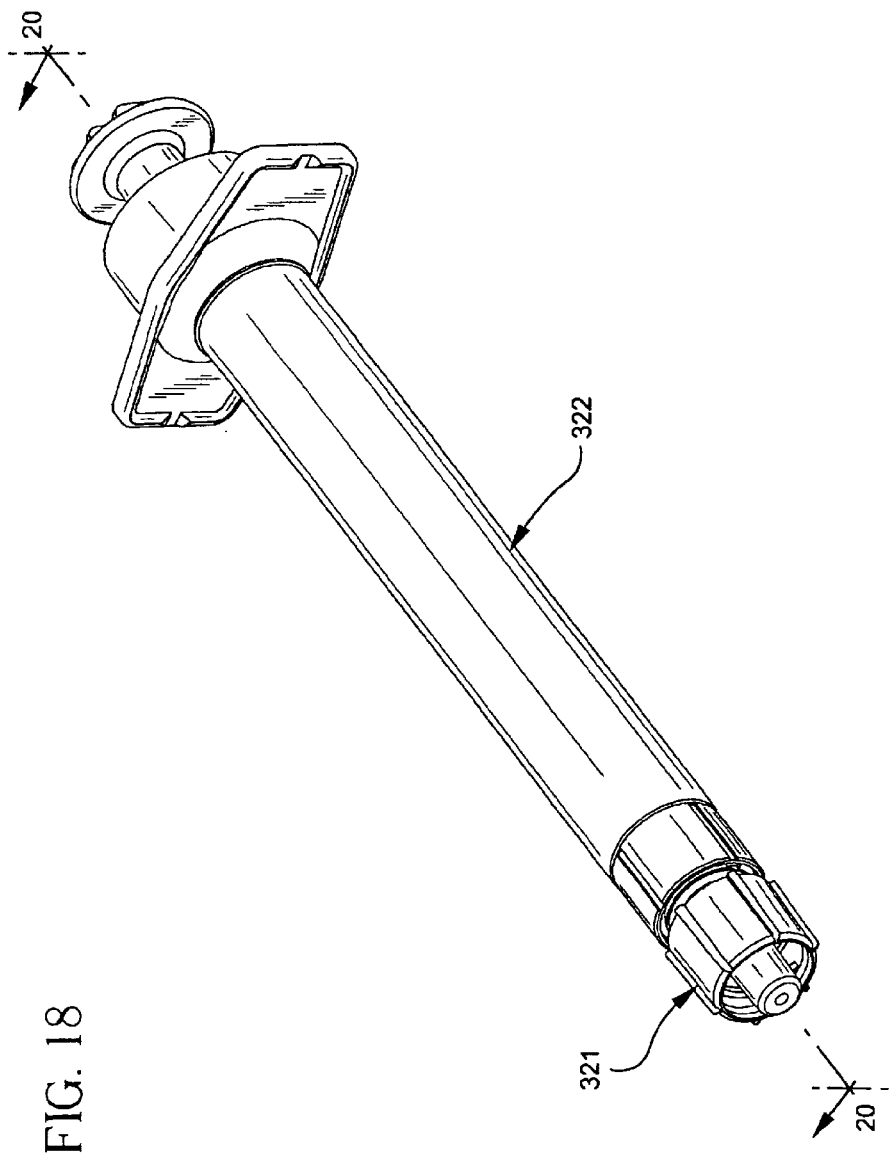
FIG. 18 is a perspective view of a fluid transfer adapter attached to a retracting needle syringe.
Figure 19:
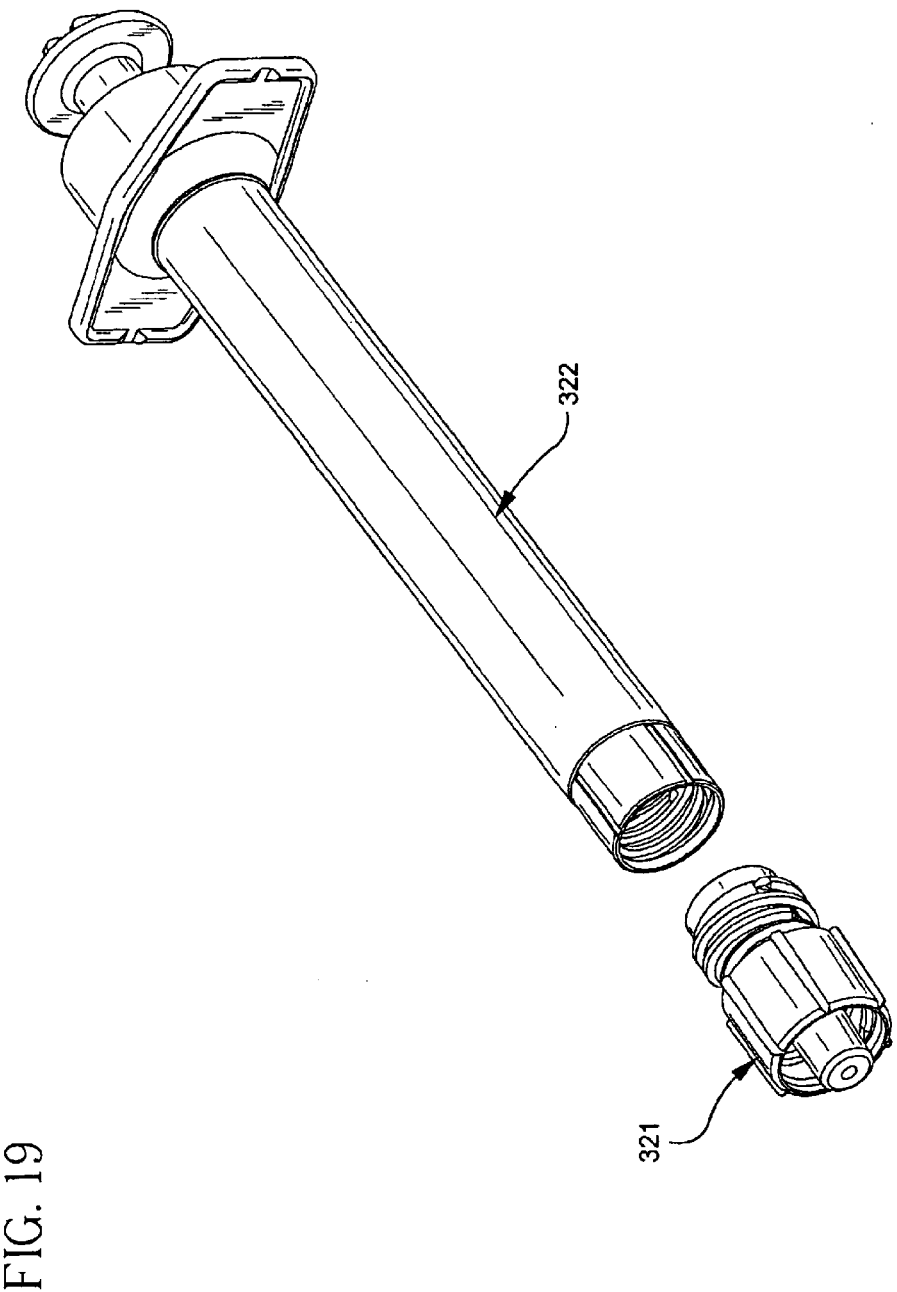
FIG. 19 is a perspective view of the syringe and adapter of FIG. 1 illustrating the adapter disconnected from the syringe barrel.

A method of making an operable retracting needle assembly 221 of the present invention comprises the steps of: providing an outer hub 253 having a proximal end 255, a distal end 256 and a passageway 257 therethrough; providing an inner hub 261 having a proximal end 262, a distal end 263 and a conduit therethrough; providing a needle cannula 271 having a distal end 273, a proximal end 274 and a lumen therethrough; providing a coil compression spring 276; assembling the inner hub, the spring and the outer hub so that the spring is compressed and held within the outer hub by the inner hub being connected to the outer hub so that the distal end of the inner hub is accessible from the passageway at the distal end of the outer hub; position proximal end 274 of cannula 271, (as best illustrated in FIG. 14) in the distal end 263 of the conduit in the inner hub; and apply adhesive 285 in the space between the conduit of the inner hub and the needle cannula. A wide variety of adhesives is suitable for attaching a cannula to a hub including epoxy adhesives which may be self-curing or curable with heat, ultraviolet light and the like.

The method of making an operable retracting needle assembly preferably further includes providing an elongated needle shield 279 and removably connecting the needle shield to outer hub 253 so that the distal end of the needle cannula is in the needle shield. At this time, the retracting needle assembly may be sealed in a package 288 which functions as a microbial barrier and sterilized along with the package using a method such as radiation sterilization, autoclaving or the like.

The method of making a retracting needle assembly may also include attaching the needle assembly to a syringe barrel 22 (see FIGS. 1–11) having an inside surface 25 defining a chamber 27, an open proximal end 28 and open distal end 29 including a cylindrical collar 31 so that outer hub 253 engages collar 31. The method may further include providing a plunger 23 either before or after the retracting needle assembly is attached to the syringe barrel. Preferably, this step occurs first before the attachment of the retracting needle assembly. This step includes providing a plunger 23 slidably positioned in fluid-tight engagement with the inside surface of said syringe barrel. At this time, the retracting needle syringe may be sealed in a package 289 which function as a microbial barrier and the package along with the retracting needle syringe is sterilized using a method such as radiation sterilization, autoclaving or the like.

Along with the many structural and functional advantages of the retracting needle assembly and retracting needle syringe of the present invention, the present invention offers a major advantage over the prior art by allowing the needle cannula to be assembled to the retracting needle assembly after the components of the needle assembly have been assembled thereby greatly reducing any potential for damaging the fragile needle tip during the assembly process.

Figure 20:
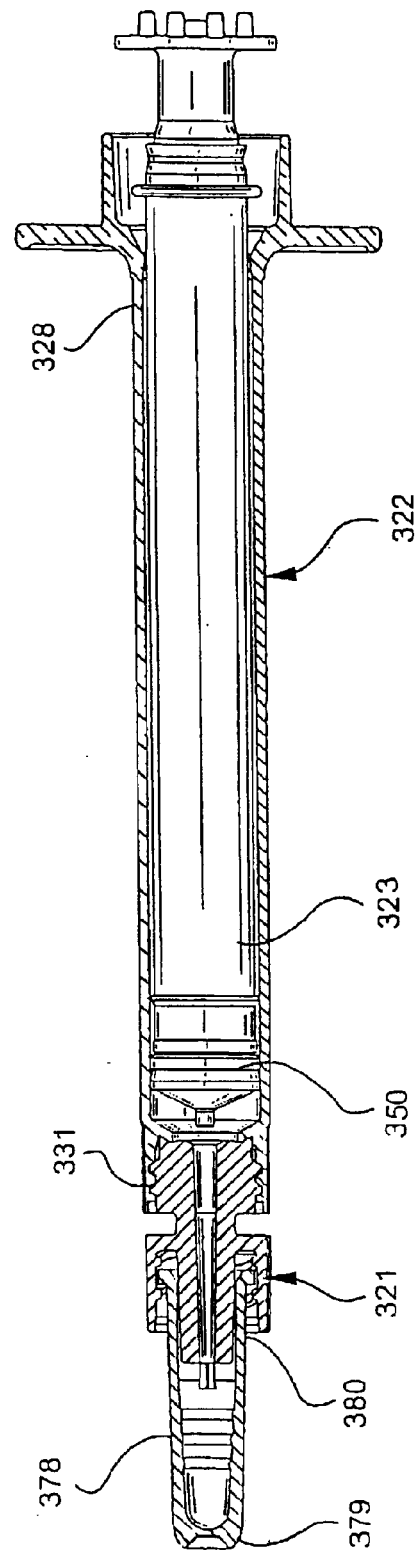
FIG. 20 is a cross-sectional view of the syringe and adapter of FIG. 18 taken along line 20—20 with a shield on the adapter
Figure 21:
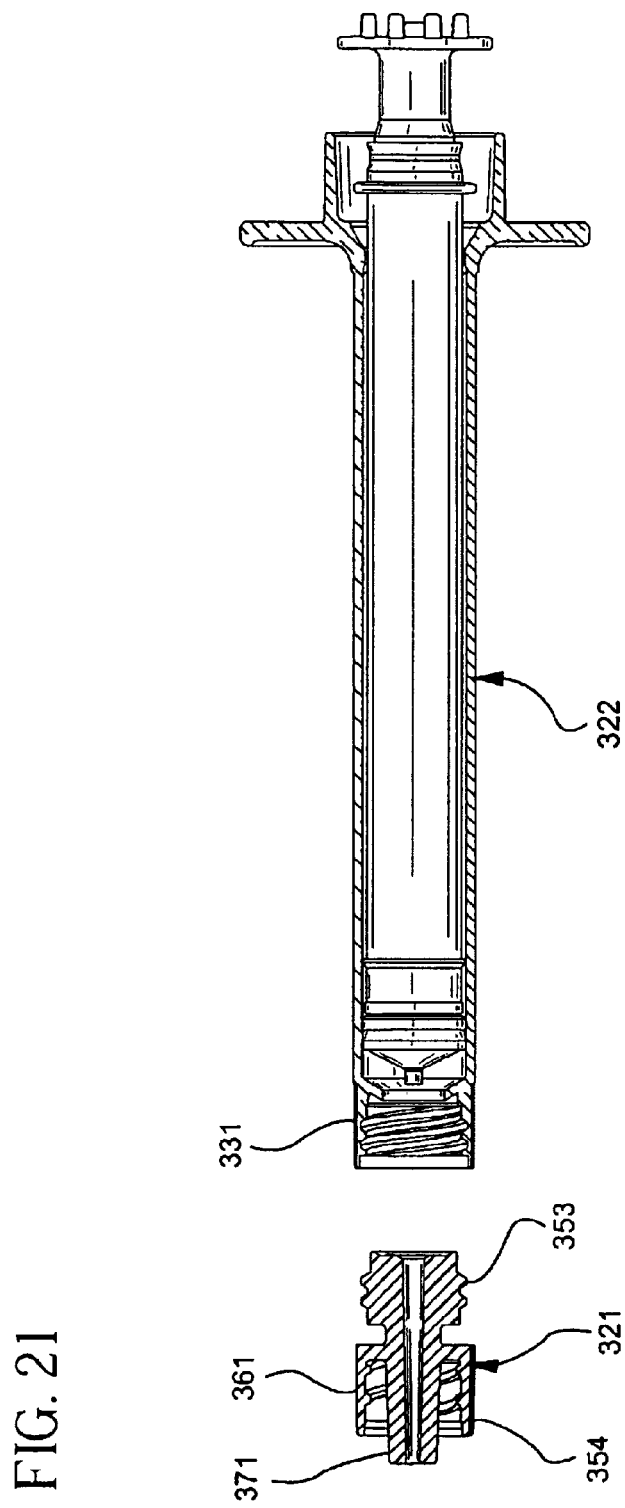
FIG. 21 is a cross-sectional view of the syringe and adapter of FIG. 20 illustrating the adapter disconnected from the syringe collar.
Figure 22:
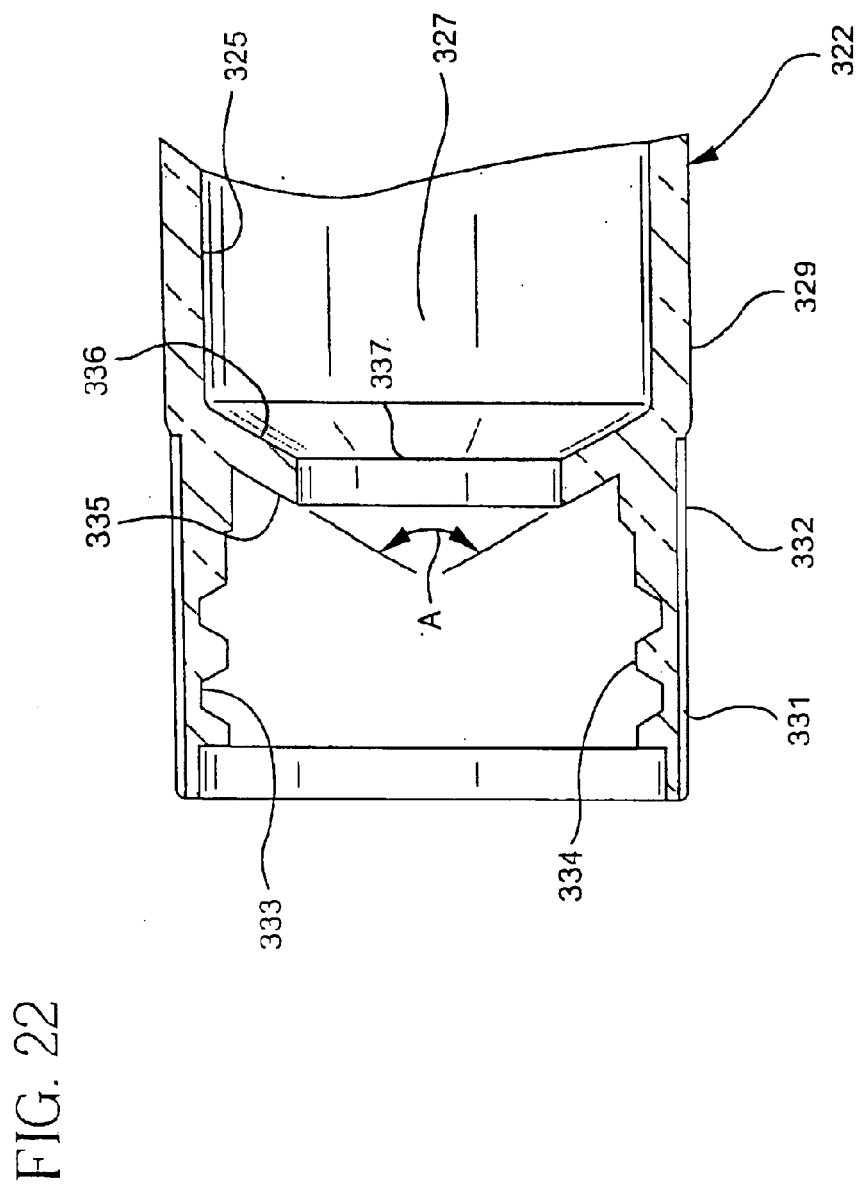
FIG. 22 is an enlarged cross-sectional view of the distal end of the syringe barrel.

Referring to FIGS. 18–26, another aspect of the present invention includes a fluid transfer adapter 321 for use with a syringe barrel 322 having an inside surface 325 defining a chamber 327, an open proximal end 328 and a distal end 329. A plunger 323 is slidably positioned in fluid-tight engagement with the inside surface 325 of the barrel 322. The plunger is the same plunger as discussed above with respect to FIGS. 1–17. A stopper seals 350 the distal end of the plunger. As shown in FIGS. 20 and 21, the stopper has a frusto-conically shaped distal end. As shown in detail in FIG. 22, the distal end 329 of the barrel includes a frusto-conically shaped edge defining a distal surface 335 and a proximal surface 336. The frusto-conically shaped edge further defines an opening 337.

A collar 331 having an outside surface 332 and an inside surface 333 extends from the distal end 329 of the barrel 322. The collar includes adapter engaging structure which in this embodiment is at least one thread 334 on the inside surface of the collar. Fluid transfer adapter 321 comprises a hub 353 having a proximal end 355, a distal end 356 and a conduit 357 therethrough. The proximal end of the conduit 357 includes a frusto-conically shaped surface 360. The conduit 357 communicates with the opening 337. As shown in FIG. 20, frusto-conically shaped surface 360 aligns with proximal surface 336 to form a straight surface when the adapter 321 is connected to the syringe. Thus, the stopper 350 cooperates with the newly formed straight surface of the proximal surface 336 and the frusto-conically shaped surface 360 of the conduit upon depression of the plunger. Moreover, the center of the stopper enters into the conduit 357. Thus, no liquid can come between the stopper and the frusto-conically shaped edge upon full depression of the plunger. The hub 353 also includes a proximally-facing frusto-conically shaped surface 359 positioned to contact distal surface 335 on the barrel to prevent liquid flow between these surfaces during normal use of the syringe.

The adapter further includes a fluid transfer element 354 which in this embodiment comprises an elongate luer tip 371 and a luer collar 361. Elongate luer tip 371 includes a distal end 373, a proximal end 374, a passageway 375 therethrough, and a tapered side wall 372 which is smaller in diameter at its distal end than at its proximal end. The proximal end of luer tip 371 is connected to the distal end of hub 353 so that passageway 375 is in fluid communication with conduit 357 of the hub.

Luer collar 361 surrounds the luer tip and includes an inside surface 362 and at least one thread 363 on the inside surface of the luer collar. The luer tip and the luer collar are sized and shaped to engage a standard female locking luer fitting contained on many fluid transfer devices for medical applications such as needle assembly 390 illustrated in FIGS. 25–26. Needle assembly 390 is representative of prior art needle assemblies available from manufacturers throughout the world. The needle assembly includes a cannula 391 having a proximal end 392, a distal end 393 and a lumen 394 therethrough. A hub 395 includes a distal end 398, an open proximal end 396 which allows access to cavity 397. The cavity has tapered sidewalls dimensioned to fit a standard luer slip tip. The hub further includes two radial thread engaging projections 399 for engaging the thread on the inside of a locking luer-type collar of a syringe barrel or other fluid transfer device. Fluid transfer adapter 321 is designed to accept standard female luer lock and luer slip type fittings found on many medical devices such as needle assembly 390. The fluid transfer adapter preferably includes an elongate needle shield 378 having a distal end 379 and an open proximal end 380 removably engaged to fluid transfer apparatus 321 so that the shield covers luer tip 371.

The retracting needle assembly of the retracting needle syringe of the present invention, due to its multiple hubs and coil spring, is more expensive to manufacture than a standard hypodermic needle assembly. Further, it is common practice when filling a hypodermic syringe to attach a hypodermic needle to the syringe and use the hypodermic needle to pierce the pierceable stopper of a medication vial in order to draw liquid medication from the vial into the syringe barrel. After the syringe is filled to the desired capacity, the needle is discarded and a retracting needle assembly or other fluid transfer adapter is attached. Also, a removable tip cap or seal may be used to protect the contents of the syringe until use.

A syringe may also be filled using a known fluid access valve assembly connected to a fluid source. The valve can be activated by a luer tip such as that on the end of a syringe or such as luer tip 371. In use the luer tip is guided into a recess in the valve assembly to establish fluid communication between the syringe and the fluid source. Fluid is then drawn into the syringe barrel by moving the syringe plunger in a proximal direction. The present invention can also be used to deliver fluid to a reservoir or other device through a fluid access valve. Due to the higher cost of a retracting needle assembly, it is not an economically sound practice to use a retracting needle assembly for the filling procedure and then throw the needle assembly away when a much lower cost standard needle assembly may be used for this procedure. The most economical way of using a retracting needle assembly is to use it at the time of injection when its retracting properties can be used. The fluid transfer adapter of the present invention allows the use of standard hypodermic needles and other fittings with the retracting needle syringe in various combinations depending on the procedure involved. The most likely use of fluid transfer adapter 321 should be using the adapter to engage a fluid access valve or another luer compatible fitting for the purpose of filling the syringe. However, the fluid transfer adapter can also be used to deliver fluid from a syringe. At the time of injection, the adapter is removed and a retracting needle assembly is installed on the syringe barrel of the retracting needle syringe. For the convenience of the user axially directed ribs 364 are provided on the luer collar to improve the user's grip on the collar for applying torque to install or remove the adapter from a syringe barrel.

Proximally facing frusto-conically shaped surface 359 is positioned and dimensioned for mating with the complementary distally facing frusto-conically shaped surface 335 on syringe barrel 322. Angle A of frusto-conically shaped surface 335 on the syringe barrel is preferably substantially similar to angle B of frusto-conically shaped surface 359 on the hub of the fluid transfer adapter. The total included angle B of frusto-conically shaped surface 359 is desirably between 3° and 178°. The total included angle B is preferably between 115° and 125° with 120° being most preferred.

Figure 23:
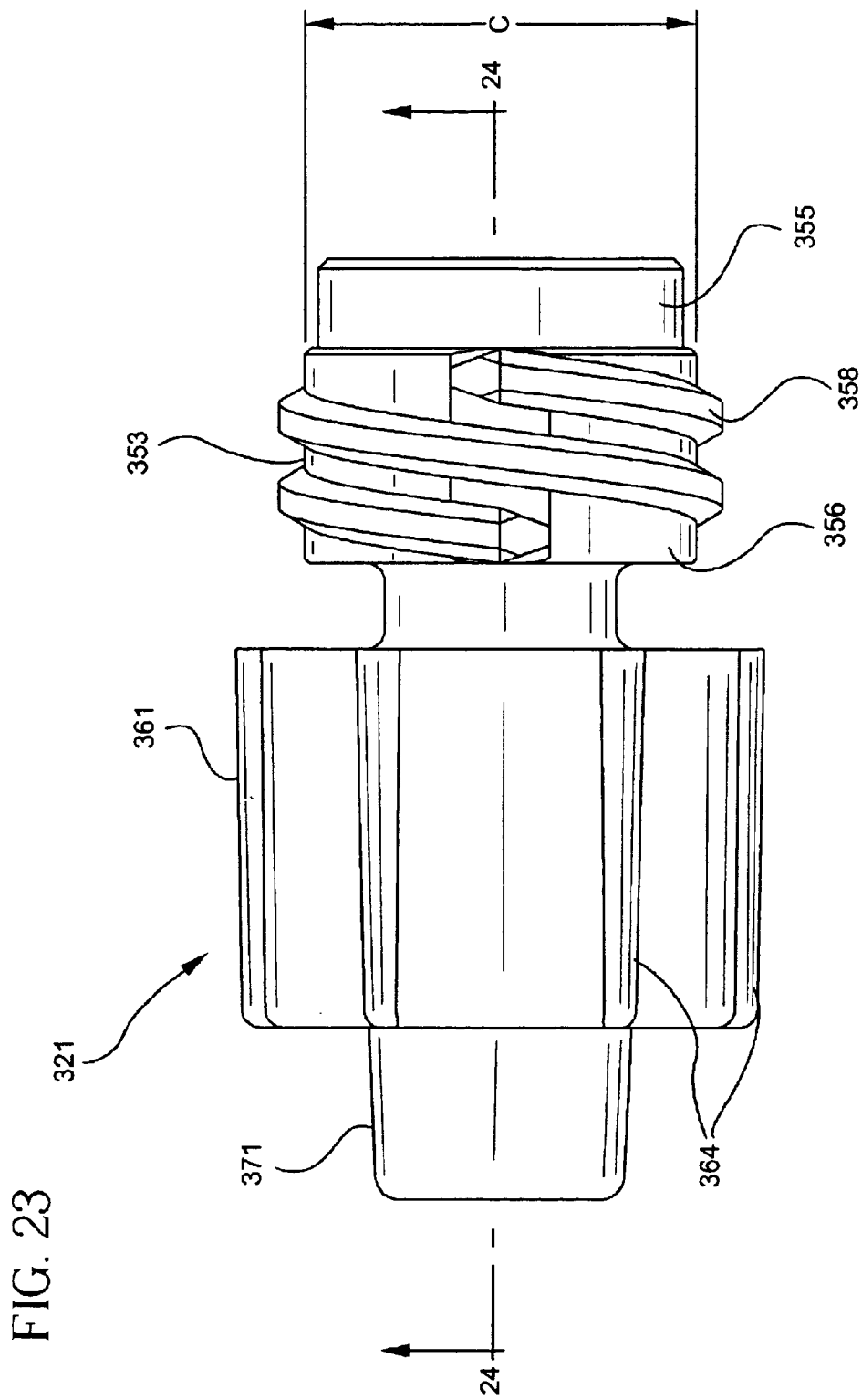
FIG. 23 is an enlarged side-elevational view of the fluid transfer adapter of the present invention.
Figure 24:
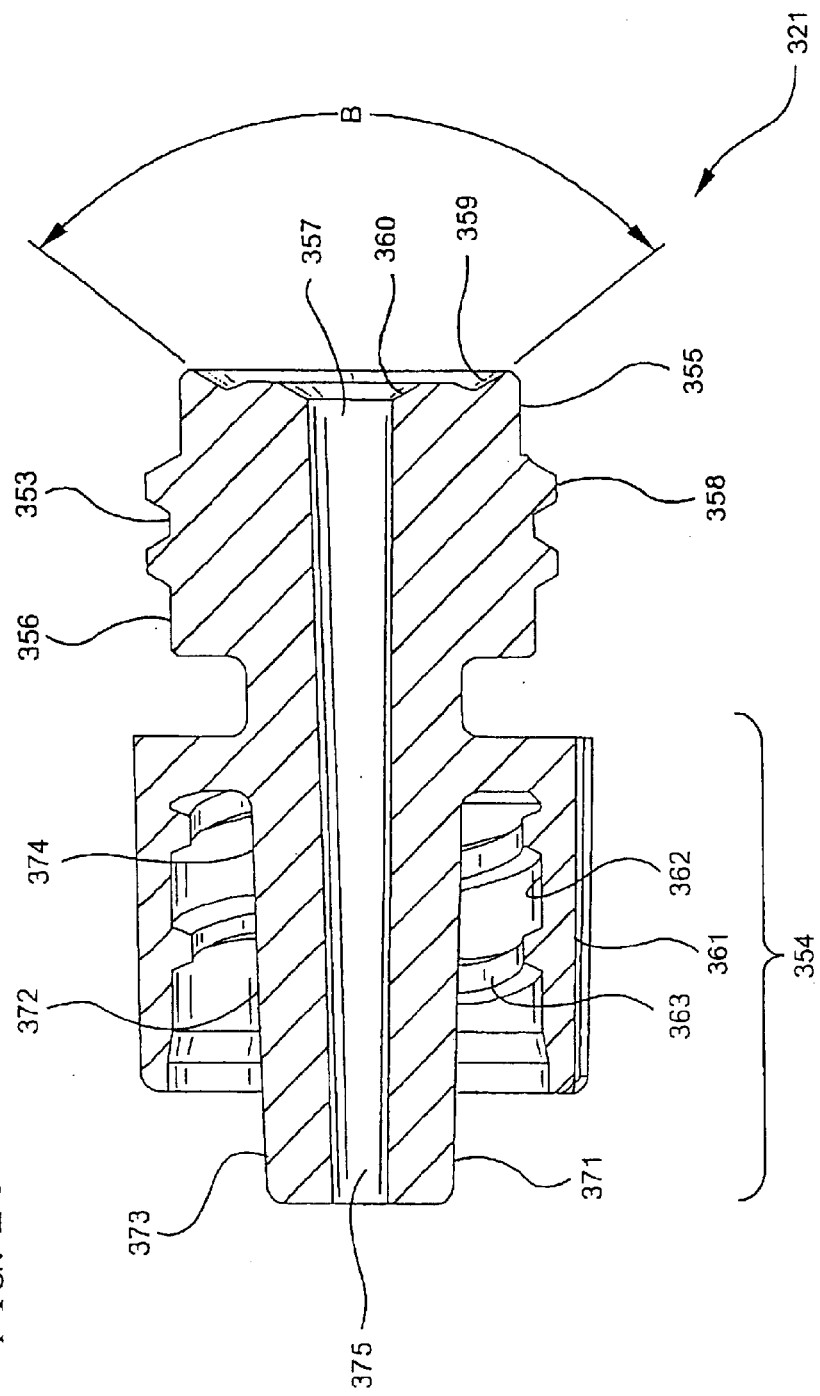
FIG. 24 is a cross-sectional view of the fluid transfer adapter of FIG. 23 taken along line 24—24.

Means for threadably engaging the hub of the adapter to the collar of the syringe barrel in this embodiment includes at least one outwardly facing thread on the hub and at least one inwardly facing thread on the collar of the syringe barrel. This arrangement is merely representative of the many possibilities within the purview of the present invention. The threads may also be inwardly facing on the hub and outwardly facing on the collar of the barrel. Threads may be right-handed or left-handed and include single or multiple leads. In the preferred embodiment thread 358 has a lead of about 3.2 mm (⅛ inch), a pitch of about 1.6 mm (1/16 inch) and a minor diameter C as illustrated in FIG. 23, equal to or less than 8.9 mm (0.35 inch). It is also within the scope of this invention to have means for threadably engaging the hub to the collar of the syringe barrel to include at least one thread engaging projection, such as radial projection 399 on the standard hypodermic needle assembly 390, on the hub to engage a thread on the collar or in the alternative, placing one or more projections on the collar for engaging a thread on the hub.

Although hub 353, and luer tip 371 and luer collar 361 of the fluid transfer element 354 can be individual components connected together, it is preferred that the hub, luer tip and collar are integrally formed, preferably of thermoplastic material.

Figure 25:
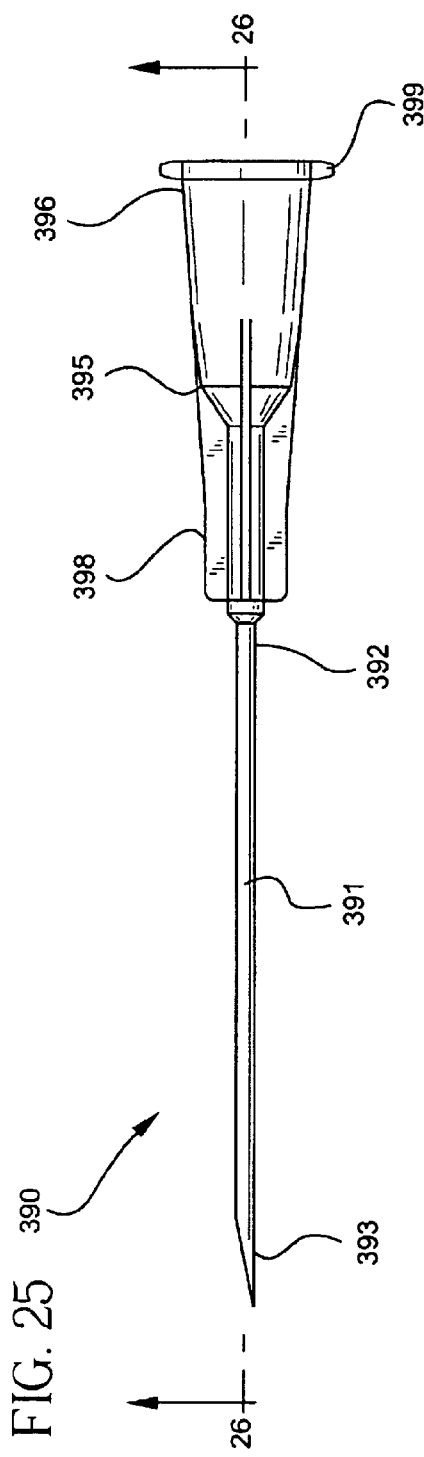
FIG. 25 is a side-elevational view of the standard hypodermic needle assembly.
Figure 26:
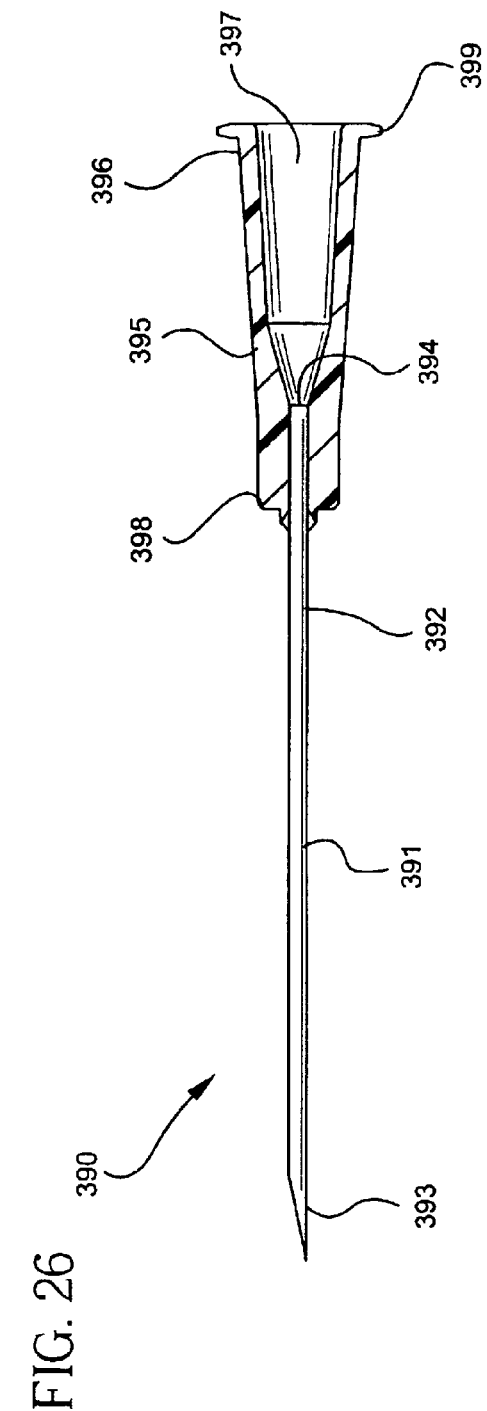
FIG. 26 is a cross-sectional view of the needle assembly of FIG. 25 taken along line 26—26.
Figure 27:
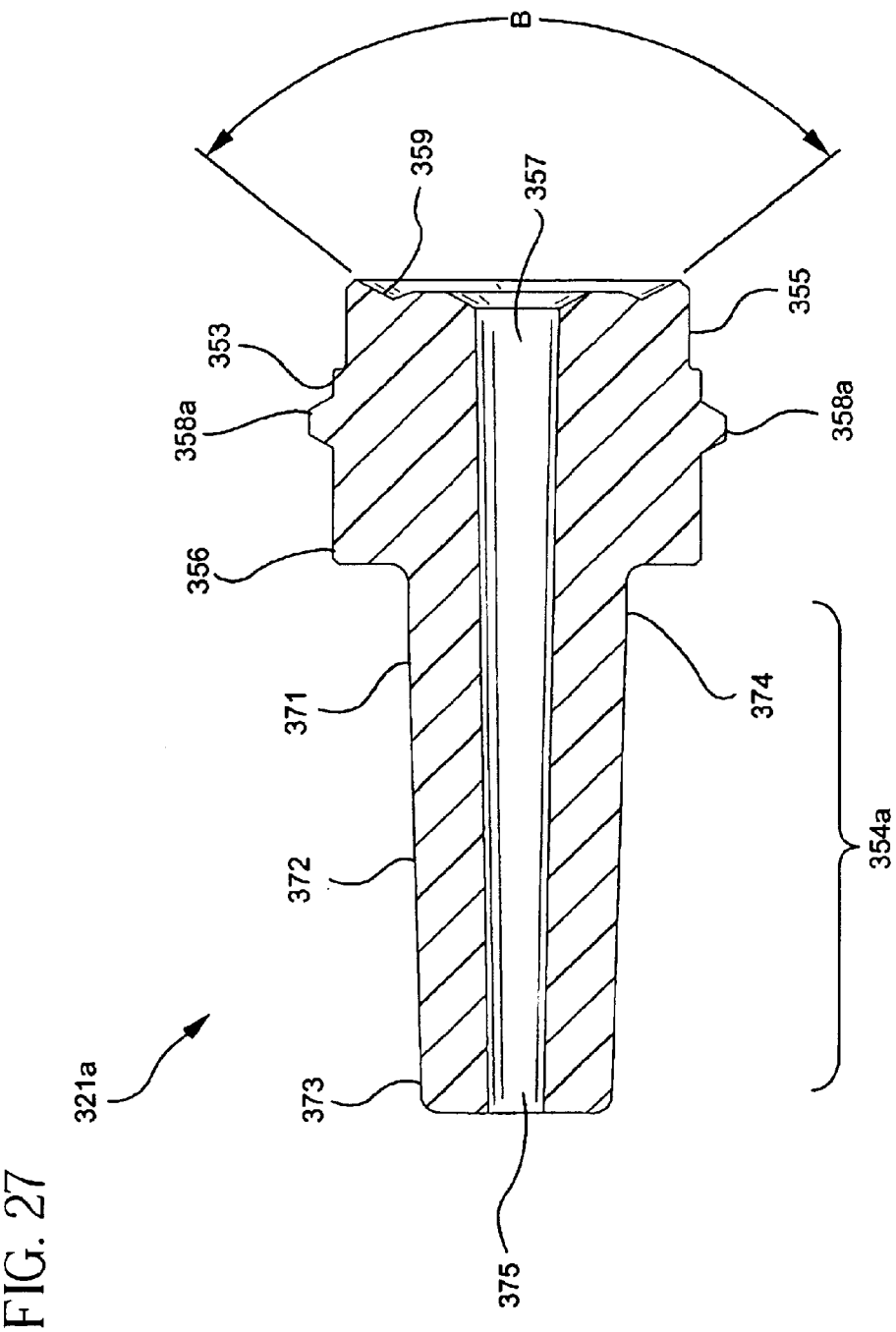
FIG. 27 is a cross-sectional view of an alternative fluid transfer adapter of the present invention.
Figure 28:
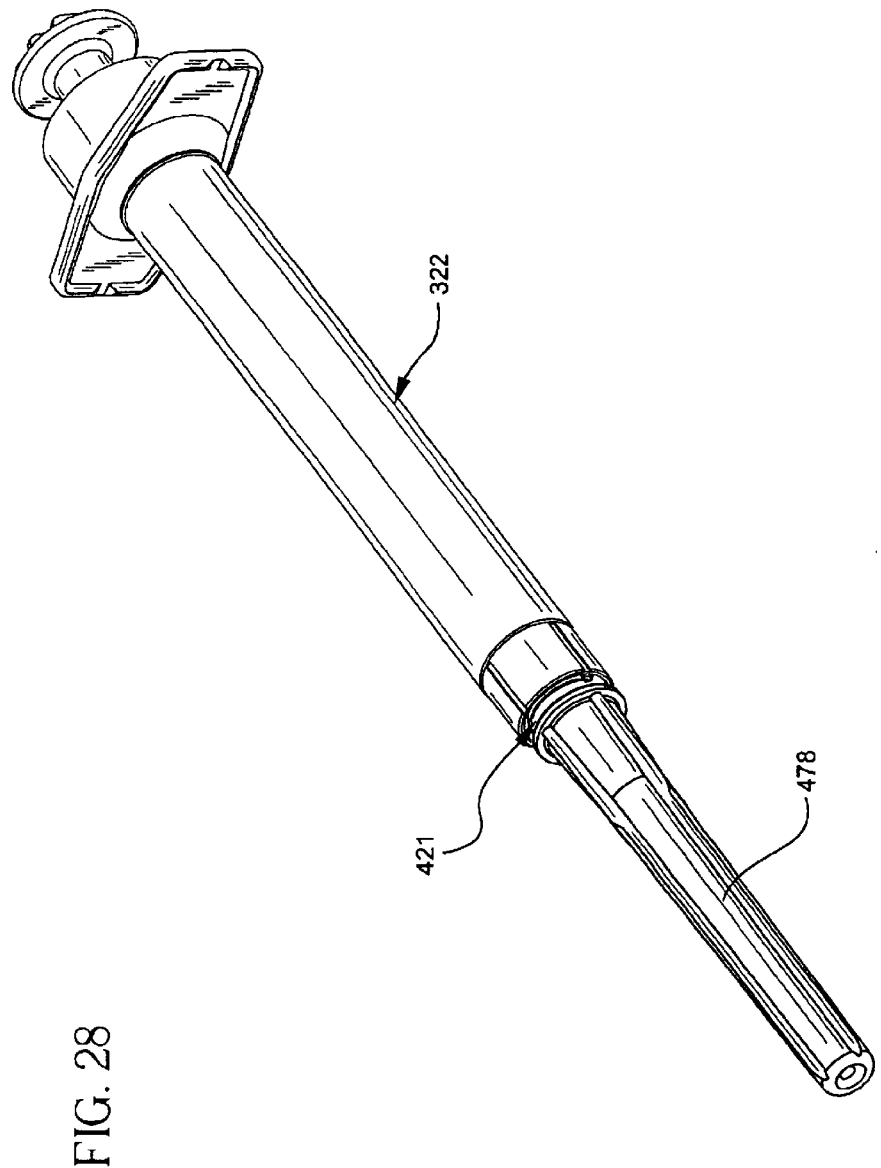
FIG. 28 is a perspective view of another alternative embodiment of the shielded fluid transfer adapter attached to a retracting needle syringe.
Figure 29:
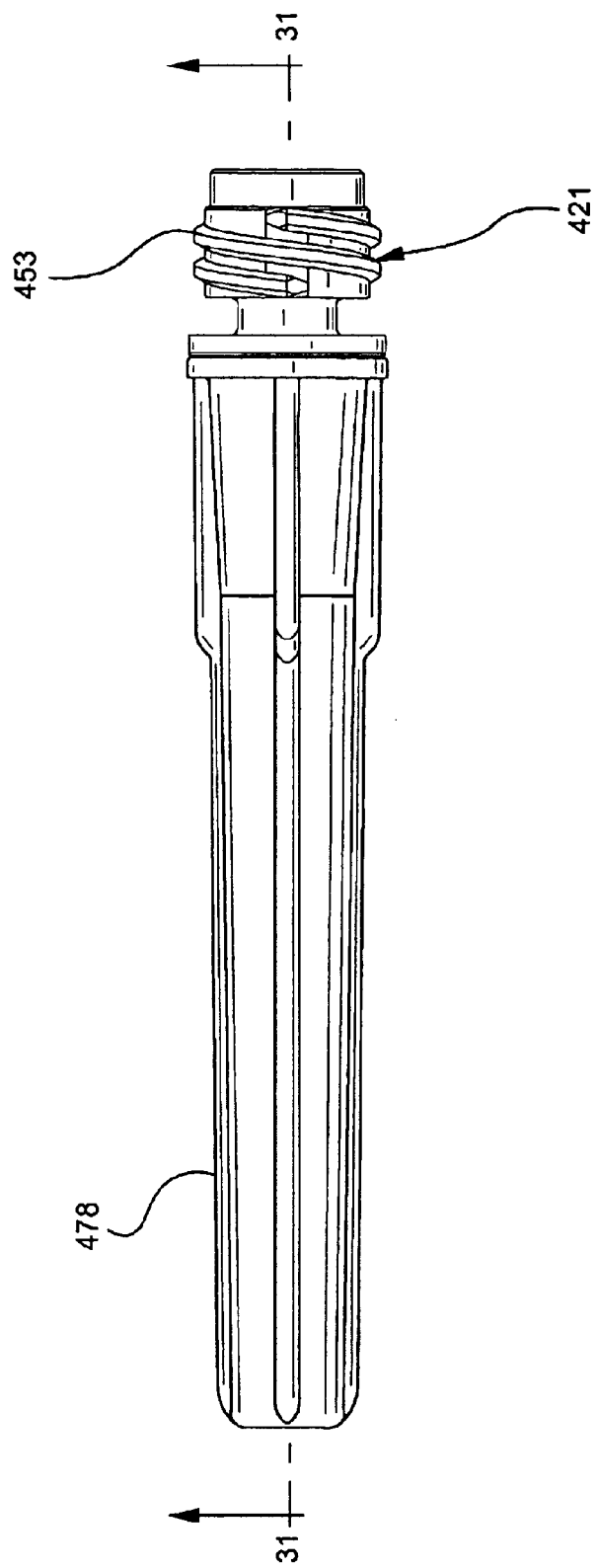
FIG. 29 is a side-elevational view of the fluid transfer adapter and shield of FIG. 27.
Figure 30:
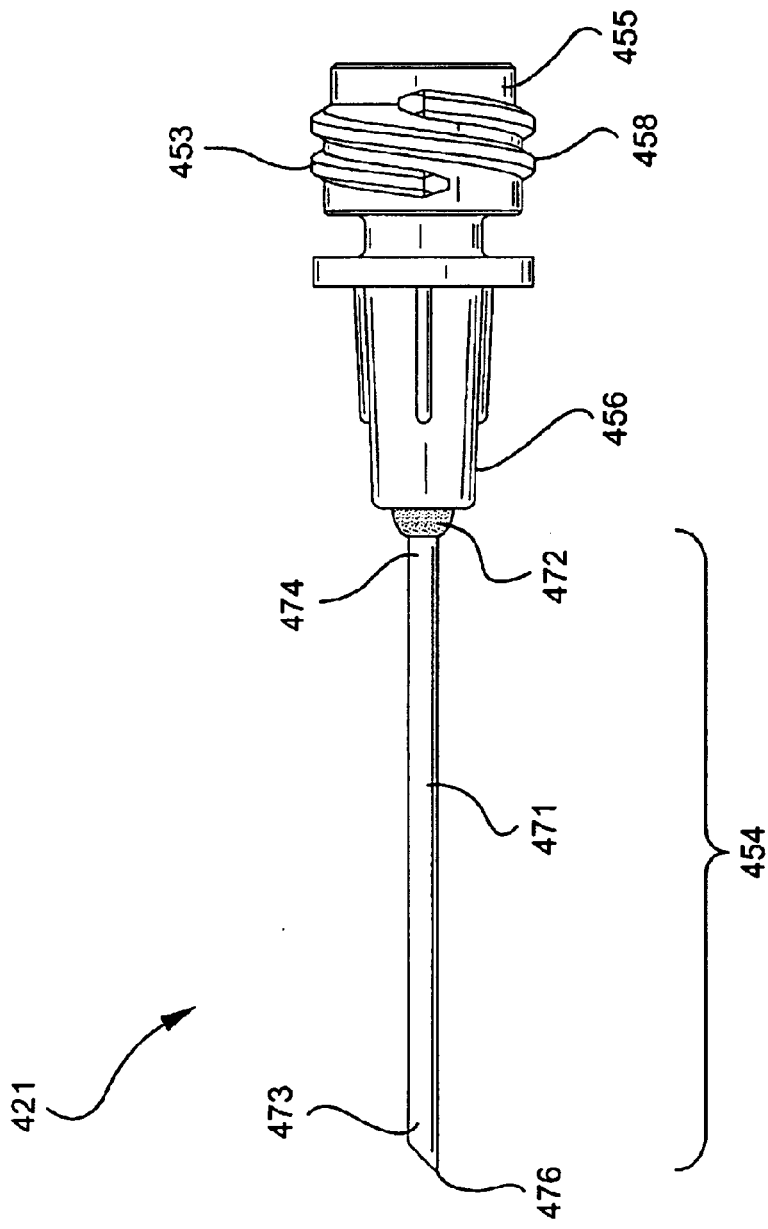
FIG. 30 is a side-elevational view of the fluid transfer adapter with shield removed.

FIG. 27 illustrates an alternative embodiment of the present invention which functions similarly to the embodiment of FIGS. 18–24. In this embodiment, fluid transfer adapter 321A includes a hub 353 and fluid transfer element 354a. The hub includes a proximal end 355, a distal end 356 and a conduit 357 therethrough. A proximally facing frusto-conically shaped surface 359 is provided for mating with the frusto-conically shaped surface of a syringe barrel such as surface 335 of syringe barrel 322 illustrated in FIG. 22. Means for threadably engaging hub 353 to the collar of a syringe barrel such as collar 331 of syringe barrel 332 illustrated in FIG. 22 includes two thread-engaging projections 358a engaging a thread on the inside of a syringe collar. Thread-engaging projections 358a functions similarly to radial projections 399 on needle hub 355 as illustrated in FIGS. 25–26. Fluid transfer element 354a in this embodiment includes an elongate luer tip 371 having a distal end 373, a proximal 374 and a passageway 375 therethrough. The proximal end of the luer tip is connected to the distal end of the hub so that the passageway is in fluid communication with the conduit of the hub. Elongate luer tip 371 includes a tapered side wall 372 which is smaller in diameter at its distal end than at its proximal end. Luer tip 371 is suited for connecting to a fluid access valve or to a luer interfacing device such as fluid sources having a female luer fitting, for the purpose of filling a syringe. The elongate luer tip of this embodiment and the elongate luer tip and luer collar of the embodiment of FIGS. 18–24 represent two of many possibilities for a fluid transfer element to be combined with the hub in the fluid transfer adapter of the present invention. Fluid transfer elements can be configured to engage a wide variety of fluid transfer connections used or usable in medical applications such as transferring medication from a reservoir to a syringe barrel or from a syringe barrel to a reservoir.

FIGS. 28–32 illustrate an alternative embodiment of the present invention which functions similarly to the embodiment of FIGS. 18–24. A fluid transfer adapter 421 of the present embodiment is for use with a syringe barrel such as syringe barrel 322 of FIGS. 18–22 having an inside surface 325 defining a chamber 327, an open proximal end 328 and an open distal end 329 including a collar 331 having apparatus engaging structure. Syringe barrel 322 also includes a distally facing frusto-conically shaped surface 335. Fluid transfer adapter 421 includes a hub 453 having a proximal end 455, a distal end 456 and a conduit 457 therethrough. The hub further includes a proximally-facing frusto-conically shaped surface 459 shaped for mating with the distally-fading frusto-conically shaped surface on the barrel. Means for threadably engaging the hub to the collar of the syringe barrel so that the frusto-conically shaped surface of the hub contacts the frusto-conically shaped surface of the barrel to prevent liquid flow between the surfaces is provided. In this embodiment the total included angle C of the frusto-conically shaped surface 459 is substantially the same as total included angle B of frusto-conically shaped surface 359 of the embodiment of FIGS.

18–24. In this embodiment means for threadably engaging the hub to the collar of the syringe barrel is similar to means for engaging the hub to a syringe barrel of the embodiment of FIGS. 18–24 and includes thread 458 for engaging complementary structure on the collar of the syringe barrel.

Fluid transfer adapter 421 includes fluid transfer element 454 having a cannula 471 with a distal end 473, a proximal end 474, and a lumen 475 therethrough. The proximal end of the cannula is connected to the distal end of the hub so that lumen 475 is in fluid communication with conduit 457.

The fluid transfer apparatus desirably includes an elongate hollow needle shield 478 having a distal end 479 and an open proximal end 480 removably engaged to hub 453 so that the shield covers cannula 471.

The desirable and preferable configurations for the thread on the hub in this embodiment are the same as those for the embodiment of FIGS. 18–24. This embodiment preferably includes cannula 471 having a sharp distal end 476 which is suitable for piercing the septum of medication containing vials for the purpose of filling the syringe. It is also desirable and within the purview of the present invention to include blunt cannulas having blunt distal ends such as blunt distal end 577 of the alternative fluid transfer adapter illustrated in FIG. 32. This embodiment also includes a hub 553 having a proximal end 555, a distal end 556 and a conduit therethrough, and a cannula 571 having a distal end 573, a proximal end 574 and a lumen therethrough. The proximal end of the cannula is connected to the distal end of the hub so that the lumen is in fluid communication with the conduit. Cannula 571 with blunt distal end 577 is for use with fluid reservoirs or transfer devices having a pre-slit septum which the blunt tip can pass through without cutting the septum. Blunt tips may also be usable for access valves to allow for fluid transfer. It is also within the purview of the present invention to include blunt cannulas having blunt distal ends wherein the end of the cannula is closed and fluid enters and exits the lumen through one or more apertures in the side of the cannula. Blunt cannulas are cannulas having variously shaped distal ends which are designed specifically to avoid accidental skin puncture during normal use. Blunt cannulas are designed to work in conjunction with injection sites having pre-slit septums. Accordingly, blunt cannulas can be shaped in any fashion that will facilitate use of pre-slit septums and still resist accidental skin puncture during normal use.

Figure 31:
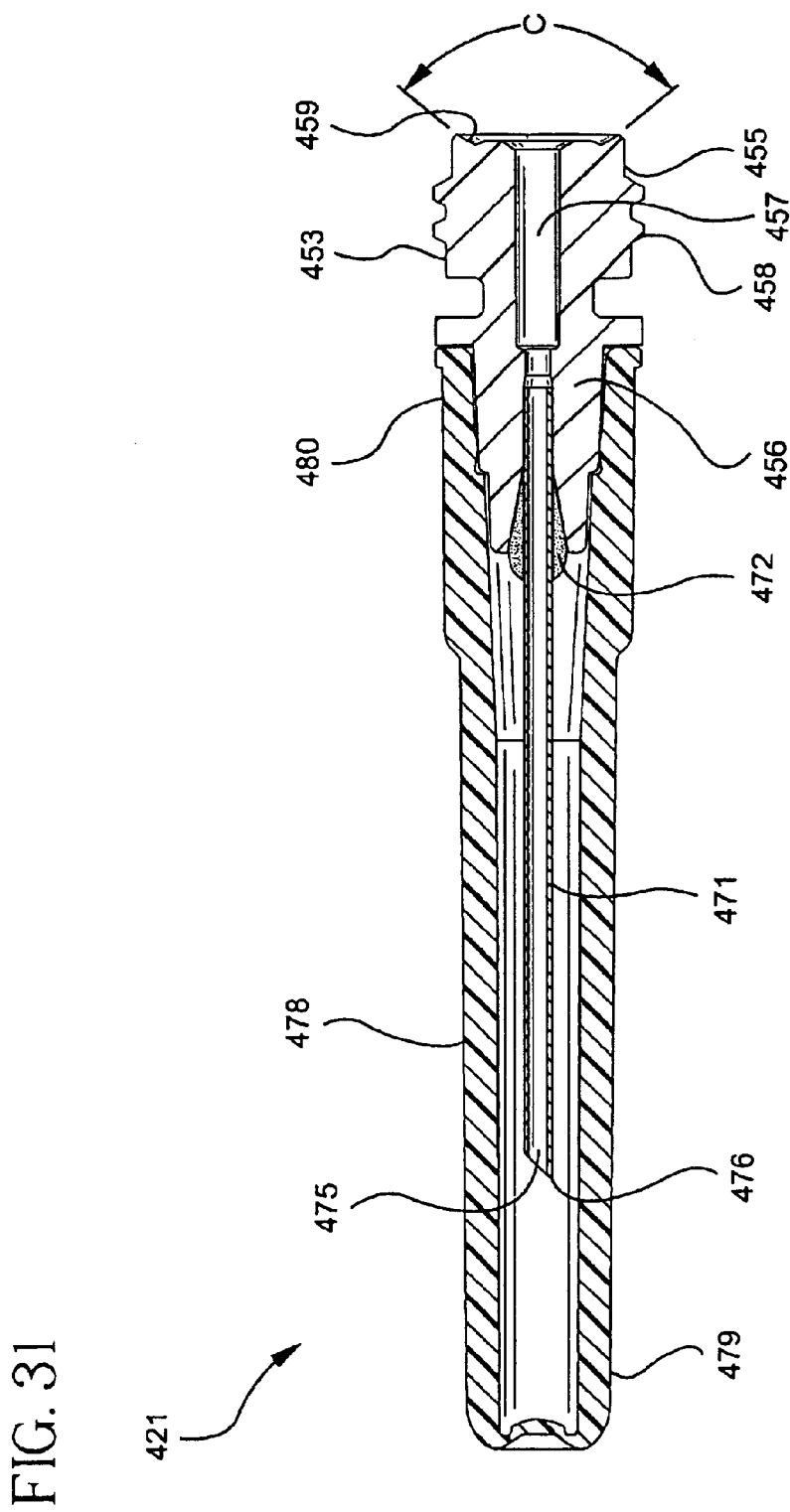
FIG. 31 is a cross-sectional view of the fluid transfer adapter and shield of FIG. 29 taken along line 31—31.
Figure 32:
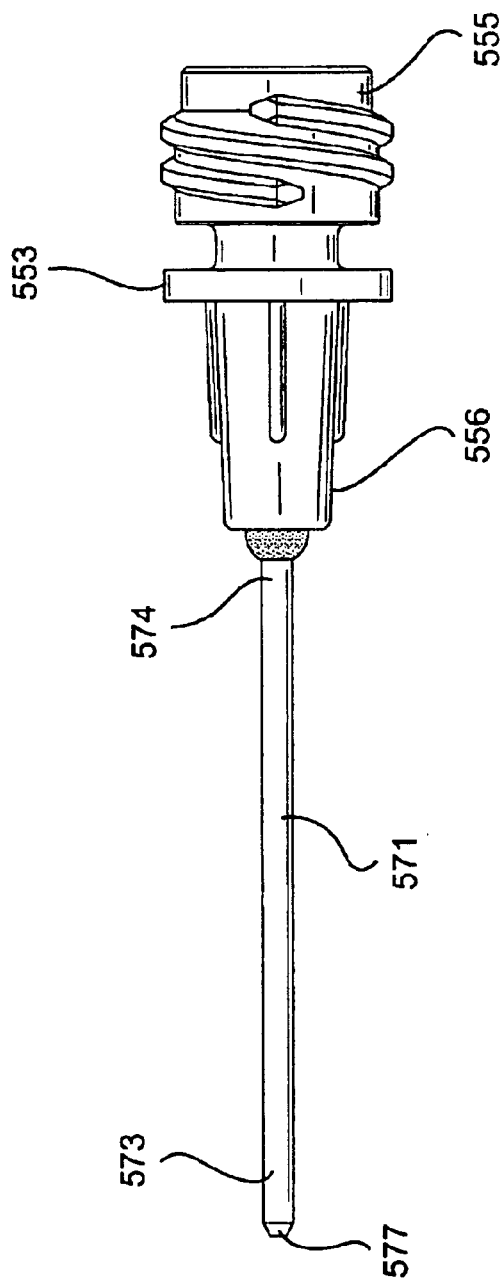
FIG. 32 is a side elevational view of another alternative embodiment of the fluid transfer adapter having a blunt cannula.

The cannula of the present embodiment may be formed of metal such as stainless steel and attached to the hub using a suitable adhesive such as epoxy 472, or, in the alternative, the hub and the cannula may be integrally formed of thermoplastic material as In the embodiment of FIG. 31.

As with the embodiment of FIGS. 18–24, the present embodiment allows for the filling of a retracting needle syringe without the use of a more expensive and complex retracting needle assembly for lower cost and avoiding accidental retraction during the filling process.

What is claimed is:

1. A fluid transfer adapter for use with a syringe barrel having an inside surface defining a chamber, an open proximal end and an open distal end including a collar having adapter engaging structure and a distally facing frusto-conically shaped edge including a distal surface and a proximal surface and a plunger including a stopper positioned for fluid tight engagement with said barrel comprising:
   a hub having a proximal end, a distal end and a conduit therethrough defining a frusto-conically shaped edge at its proximal end, and a proximally-facing frusto-conically shaped surface for mating with said distal surface of said frusto-conically shaped edge of said barrel, wherein upon mating said adapter with said syringe barrel, said frusto-conically shaped edge of said conduit aligns with said proximal surface to form a flat surface so that said stopper abuts said flat surface upon full depression of said plunger;
   means for threadably engaging said hub to said collar so that said frusto-conically shaped surface of said hub contacts said frusto-conical surface of said barrel; and
   a fluid transfer element including an elongate luer tip having a distal end, a proximal end, and a passageway therethrough, said proximal end of said luer tip being connected to said distal end of said hub so that said passageway is in fluid communication with said conduit.

2. The adapter of claim 1 wherein said fluid transfer element further includes a luer collar surrounding said luer tip having an inside surface, at least one thread on said inside surface, said luer tip and luer collar being sized and shaped to engage a standard female luer fitting.

3. The adapter of claim 1 further including an elongate hollow shield having a distal end and an open proximal end removably engaged to said adapter so that said shield covers said luer tip.

4. The adapter of claim 2 wherein said hub, said luer tip and said luer collar are integrally formed of thermoplastic material.

5. The adapter of claim 1 wherein said means for threadably engaging said hub to said collar includes at least one thread on said hub.

6. The adapter of claim 5 wherein said at least one thread is a right hand thread.

7. The adapter of claim 5 wherein said at least one thread is a multiple lead thread.

8. The adapter of claim 5 wherein said at least one thread has a lead of 3.2 mm (⅛ inch).

9. The adapter of claim 5 wherein said at least one thread has a pitch of 1.6 mm (1/16 inch).

10. The adapter of claim 5 wherein the root diameter of said at least one thread is equal or less than 8.9 mm (0.35 inch).

11. The adapter of claim 1 wherein said frusto-conically shaped edge has a total included angle of 3° to 178°.

12. The adapter of claim 1 wherein said frusto-conically shaped edge has a total included angle of 115° to 125°.

13. The adapter of claim 1 wherein said frusto-conically shaped edge has a total included angle of 120°.

14. The adapter of claim 1 wherein said means for threadably engaging said hub to said collar includes at least one thread engaging projection on said hub.

15. A fluid transfer apparatus comprising:
   a syringe barrel having an inside surface defining a chamber, an open proximal end and an open distal end including a collar having adapter engaging structure and a distally facing frusto-conically shaped edge including a distal surface and a proximal surface; and
   a fluid transfer adapter including a hub threadably engaged with said collar, said hub having a proximal end, a distal end, a conduit therethrough defining a frusto-conically shaped edge at its proximal end, and a proximally-facing frusto-conically shaped surface mating with said distal surface on said barrel, and a fluid transfer element having a distal end, a proximal end, and a passageway therethrough, said proximal end of said fluid transfer element being connected to said distal end of said hub so that said passageway is in fluid communication with said conduit, wherein said frusto-conically shaped edge of said conduit aligns with said proximal surface to form a surface.

16. The apparatus of claim 15 wherein said fluid transfer element is an elongate cannula.

17. The apparatus of claim 16 wherein said hub and said cannula are integrally formed of thermoplastic material.

18. The apparatus of claim 16 wherein said cannula includes a blunt distal tip.

19. The apparatus of claim 16 wherein said cannula is formed of metal.

20. The apparatus of claim 15 wherein said fluid transfer element is an elongate luer tip having a tapered side wall being smaller in diameter at its distal end than at its proximal end.

21. The apparatus of claim 20 wherein said fluid transfer element further includes a luer collar surrounding said luer tip having an inside surface, at least one thread on said inside surface, said luer tip and luer collar being sized and shaped to engage a standard female luer fitting.

22. The apparatus of claim 15 further including at least one thread on said hub engaging said collar.

23. The apparatus of claim 22 wherein said at least one thread is a right-hand thread.

24. The apparatus of claim 22 wherein said at least one thread is a multiple lead thread.

25. The apparatus of claim 22 wherein said at least one thread has a lead of 3.2 mm (⅛ inch).

26. The apparatus of claim 22 wherein said at least one thread has a pitch of 1.6 mm (1/16 inch).

27. The apparatus of claim 22 wherein the minor diameter of said at least one thread is equal or less than 8.9 mm (0.35 inch).

28. The apparatus of claim 15 wherein said frusto-conically edge surface has a total included angle of 6° to 178°.

29. The apparatus of claim 15 wherein said frusto-conically shaped edge has a total included angle of 115° to 125°.

30. The apparatus of claim 15 wherein said frusto-conically shaped edge has a total included angle of 120°.

31. The apparatus of claim 15 further including a plunger slidably positioned in fluid-tight engagement with said inside surface of said barrel.

* * * * *